US012769874B2

(12) United States Patent
Gonzalez Cervantes et al.

(10) Patent No.: US 12,769,874 B2
(45) Date of Patent: Oct. 20, 2026

(54) SECURE STORAGE AND RETRIEVAL OF SENSITIVE INFORMATION

(71) Applicant: Apple Inc., Cupertino, CA (US)

(72) Inventors: Pablo Antonio Gonzalez Cervantes, San Jose, CA (US); Mohan Singh Randhava, San Carlos, CA (US); Jorge F. Pozas Trevino, Emerald Hills, CA (US); Samuel A Mussell, Sunnyvale, CA (US); Isaac Pinol Catadau, Union City, CA (US); Steven A. Myers, San Jose, CA (US); Dongsheng Zhang, Mountain View, CA (US); Suhail Ahmad, Los Altos, CA (US); Zhengjun Jiang, San Jose, CA (US); Yannick L. Sierra, San Francisco, CA (US); Amir H. Jadidi, San Ramon, CA (US)

(73) Assignee: Apple Inc., Cupertino, CA (US)

( * ) Notice: Subject to any disclaimer, the term of this patent is extended or adjusted under 35 U.S.C. 154(b) by 26 days.

(21) Appl. No.: 18/818,115

(22) Filed: Aug. 28, 2024

(65) Prior Publication Data

US 2024/0419842 A1 Dec. 19, 2024

Related U.S. Application Data

(63) Continuation of application No. 18/377,478, filed on Oct. 6, 2023, now Pat. No. 12,079,370, which is a (Continued)

(51) Int. Cl.
*G06F 21/62* (2013.01)
*G16H 10/60* (2018.01)

(Continued)

(52) U.S. Cl.
CPC ......... *G06F 21/6245* (2013.01); *G16H 10/60* (2018.01); *H04L 9/0825* (2013.01); *H04L 9/0866* (2013.01); *H04L 9/14* (2013.01)

(58) Field of Classification Search
CPC .................................................. G06F 21/6245
See application file for complete search history.

(56) References Cited

U.S. PATENT DOCUMENTS 11,790,113 B2 10/2023 Gonzalez Cervantes et al.
12,079,370 B2 9/2024 Gonzalez Cervantes et al.

(Continued)

FOREIGN PATENT DOCUMENTS

CN 104704527 A 6/2015

OTHER PUBLICATIONS

U.S. Appl. No. 17/343,358 , Notice of Allowance, Mailed On Jul. 6, 2023, 21 pages.

(Continued)

*Primary Examiner* — Bradley W Holder
(74) *Attorney, Agent, or Firm* — Kilpatrick Townsend & Stockton LLP

(57) ABSTRACT

Techniques for storing health data can include a multi-node data structure. A data node, a category node, and an institution node of a multi-node data structure can be generated in accordance with a configuration file. The data node can include health data and can be identified by a first unique data identifier and encrypted using a first cryptographic key. The category node can include the first unique data identifier and the first cryptographic key. The category node can be identified by a second unique data identifier and encrypted using a second cryptographic key. The institution node can include the second unique data identifier and the second cryptographic key. The institution node can be identified by a third unique data identifier and encrypted using a third (Continued)

cryptographic key. The data node, the category node, and the institution node can be shared with a service provider.

17 Claims, 13 Drawing Sheets

Related U.S. Application Data continuation of application No. 17/343,358, filed on Jun. 9, 2021, now Pat. No. 11,790,113.

(60) Provisional application No. 63/064,811, filed on Aug. 12, 2020.

(51) Int. Cl.
*H04L 9/08* (2006.01)
*H04L 9/14* (2006.01)

(56) References Cited

U.S. PATENT DOCUMENTS

| | | | | |
|---|---|---|---|---|
| 2012/0059668 | A1 | 3/2012 | Baldock et al. | |
| 2012/0239432 | A1 | 9/2012 | Desai | |
| 2013/0006867 | A1* | 1/2013 | Dove | H04L 9/083 707/827 |
| 2014/0297301 | A1* | 10/2014 | Rock | G06Q 10/103 705/2 |
| 2015/0161413 | A1 | 6/2015 | Calem et al. | |
| 2015/0213570 | A1 | 7/2015 | Li et al. | |
| 2020/0057867 | A1* | 2/2020 | Aunger | H04L 63/0428 |
| 2020/0327250 | A1* | 10/2020 | Wang | G06N 20/00 |

OTHER PUBLICATIONS

U.S. Appl. No. 18/377,478 , Notice of Allowance, Mailed On May 1, 2024, 12 pages.
International Application No. PCT/US2021/044974 , International Preliminary Report on Patentability, Mailed On Feb. 23, 2023, 8 pages.
International Application No. PCT/US2021/044974 , International Search Report and Written Opinion, Mailed On Nov. 11, 2021, 11 pages.
European Patent Application No. EP21762894.0 , Office Action, Mailed On Apr. 29, 2025, 7 pages.
Chinese Patent Application No. CN202180056367.3, Office Action, Mailed On Jul. 20, 2026, 17 pages (8 pages of English translation and 9 pages of official language copy).

* cited by examiner

SECURE STORAGE AND RETRIEVAL OF SENSITIVE INFORMATION

CROSS-REFERENCES TO RELATED APPLICATIONS

This application is a continuation of U.S. patent application Ser. No. 18/377,478, filed Oct. 6, 2023, which is a continuation of U.S. patent application Ser. No. 17/343,358, filed Jun. 9, 2021, which claims priority to U.S. Provisional Application Ser. No. 63/064,811, filed Aug. 12, 2020, which are hereby incorporated by reference in their entirety for all purposes.

BACKGROUND

Advancements have been made in recent years that allow users to download, from remote electronic health record (EHR) systems, health data to their mobile user devices. For example, a user may use their smartphone to connect to an endpoint of the EHR system and download a copy of their clinical health record.

BRIEF SUMMARY

According to some implementations, a method may include encrypting, by a mobile user device using a plurality of cryptographic keys, health data associated with a user account of the mobile user device; storing the encrypted health data on the mobile user device using a multi-node data storage structure, with each node of the multi-node data structure being identified by a unique data identifier; sending the encrypted health data to a service provider that stores the encrypted health data according to the multi-node data storage structure, the unique data identifier identifying at least one node of the multi-node data storage structure; receiving a selection of a health institution to receive at least a portion of the health data; and based at least in part on the selection, sending at least one cryptographic key of the plurality of cryptographic keys and a data identifier corresponding to the multi-node storage structure to an electronic health record system associated with the health institution, the electronic health record system enabled to use the at least one cryptographic key and the data identifier to access and decrypt the portion of the health data from the service provider.

According to some implementations, a mobile user device may include one or more memories; and one or more processors, communicatively coupled to the one or more memories, configured to: send encrypted health data to a service provider that stores the encrypted health data according to a multi-node data storage structure, the encrypted health data stored on the mobile user device according to a first version of the multi-node data storage structure; receive a selection of a health institution to receive at least a portion of the health data; and based at least in part on the selection, send a cryptographic key and a data identifier that identifies a storage node of the first version of the multi-node storage structure to an electronic health record system associated with the health institution, the electronic health record system enabled to use the cryptographic key and the data identifier to access and decrypt the portion health data stored by the service provider at the storage node.

According to some implementations, a method may include receiving an upload request from a mobile user device, the upload request including encrypted health record data and a set of unique data identifiers corresponding to the encrypted health record data; storing, in a secure storage, the encrypted health record data in accordance with the set of unique data identifiers; receiving a query from an electronic health record system associated with a health institution, the query including at least one unique data identifier of the set of unique data identifiers; retrieving, from the secure storage using the at least one unique data identifier, the encrypted health record data; and sending the encrypted health record data for viewing by the electronic health record system of the health institution system.

According to some implementations, a method may include generating a data node of a multi-node data structure in accordance with a configuration file, the data node identified by a first unique data identifier and encrypted using a first cryptographic key, the data node including health data; generating a category node of the multi-node data structure in accordance with the configuration file, the category node including the first unique data identifier and the first cryptographic key, the category node identified by a second unique data identifier and encrypted using a second cryptographic key; generating an institution node of the multi-node data structure in accordance with the configuration file, the institution node including the second unique data identifier and the second cryptographic key, the institution node identified by a third unique data identifier and encrypted using a third cryptographic key; and sharing the data node, the category node, and the institution node with a service provider.

DETAILED DESCRIPTION

Figure 1:
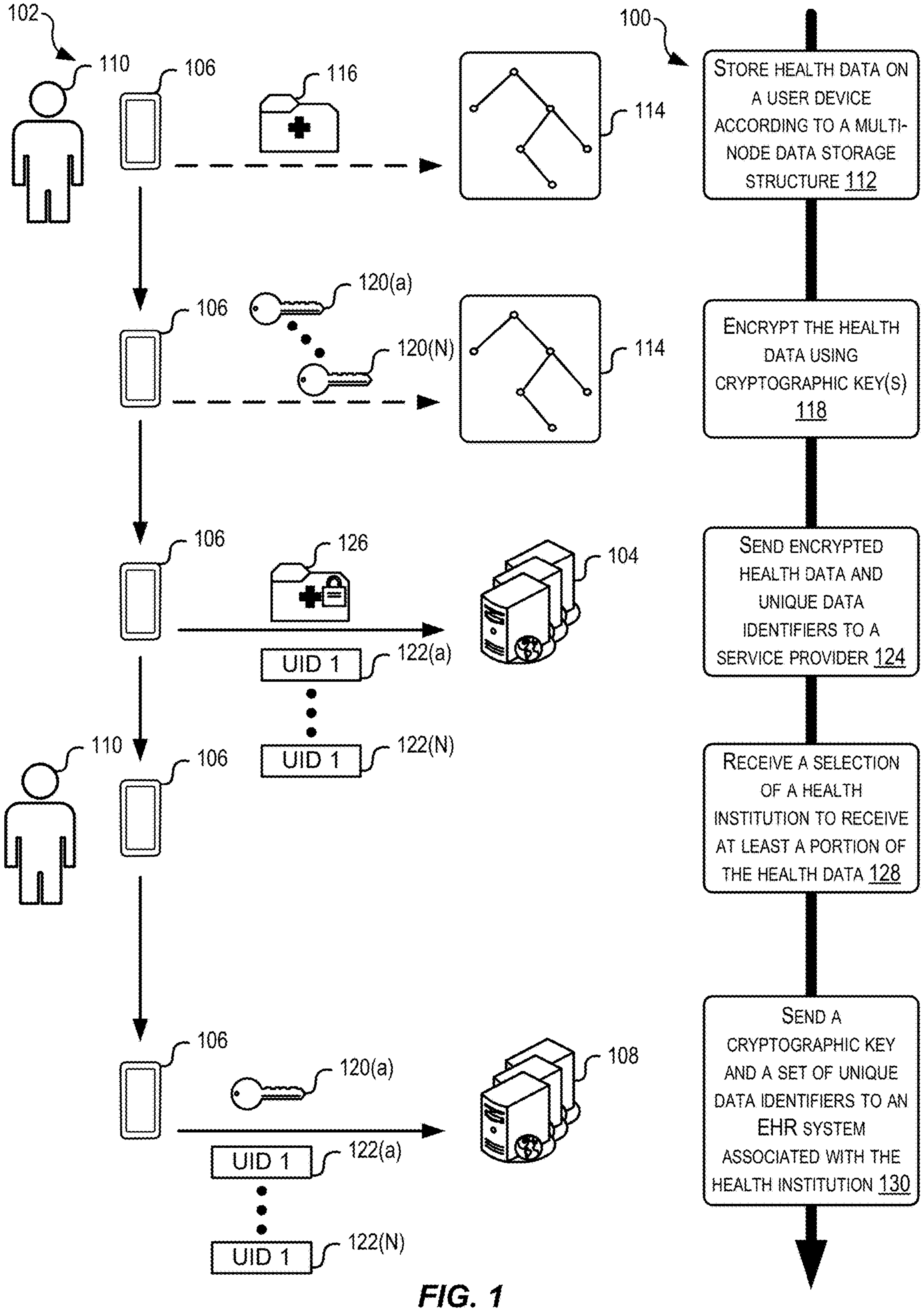
FIG. 1 illustrates a block diagram and a flowchart showing an example process for sharing health data from user devices with electronic health record systems, according to at least one example.

In the following description, various examples will be described. For purposes of explanation, specific configurations and details are set forth in order to provide a thorough understanding of the examples. However, it will also be apparent to one skilled in the art that the examples may be practiced without the specific details. Furthermore, well-known features may be omitted or simplified in order not to obscure the example being described.

Examples of the present disclosure are directed to, among other things, a health data sharing platform that includes methods, systems, devices, and computer-readable media that allow a user to make portions of sensitive health data available for querying by users of a health institution. The health data may have been previously downloaded to the user device from the same or a different health institution, generated by or input at the user device, and/or collected from one or more accessory devices (e.g., a smart watch, wearable device).

The user device functions as the source of truth for the health data. Any health data that is sent from the user device is stored in a multi-node data storage structure, with each node and corresponding data elements being encrypted using a unique cryptographic key. The health data sharing platform described herein provides a mechanism for a user to securely share their health data with a third-party (e.g., a health institution) that includes end-to-end encryption, in a summarized manner that conserves bandwidth and optimizes storage capacity and storage access, and ensures data privacy and identity privacy of the sharing user. The mechanism additionally ensures that the data is authenticated to the sharing user and enables querying by authorized users of the health institutions. Because of the data structure used to store the health data and the unique sharing arrangement described herein, the querying is optimized, resulting in client and server operating more efficiently than other devices that query health data using different platforms. In some examples, the techniques described herein may enable sharing of health data between users that are not associated with a health institution and are not generating health data on behalf of the user (e.g., family members, caregivers, etc.).

As described in detail herein, to maintain data security, a user device, not a remote server, encrypts health data using cryptographic key information and generates data identifier information. To additionally maintain data security, the user device shares the cryptographic key information and the data identifier information with an EHR system of the health institution, but does not share the actual health data. Instead, the user device shares the encrypted health data along with the data identifier information, but not the cryptographic key information, with a cloud-based service provider that can be trusted to securely store the information. To view the health data, a web-based application of the EHR system queries the cloud-based service provider using the data identifier information. Because the EHR system also includes the cryptographic key information, the web-based application is enabled to decrypt the portions of the health data. The health data is stored only in memory on the user device hosting the web application such that when the session ends, the data no longer persists. This helps to maintain data privacy and data security. Additionally, because the cloud-based service provider does not have the cryptographic key information, it is unable to decrypt and view any of the health data. Considering this and that the health data is also stored using multiple cryptographic keys to encrypt a multi-node data storage structure, the cloud-based service provider would be unable to identify the user to whom the health data belongs. Thus, user privacy is protected.

Turning now to a particular example, a cardiologist at a health intuition who is treating a patient may be interested in viewing heart rate data for the patient (e.g., data for some historical period) that has been collected by the patient's smartwatch and shared with the patient's smartphone. The patient may use an application on their smartphone to search for and identify the health institution to which the cardiologist belongs (e.g., "Regional Hospital"). The patient may select an option to share health data with Regional Hospital. If not previously encrypted, at this point, the smartphone may query the health data stored on the device to identify and encrypt relevant portions. For example, the smartphone may reference a configuration file to identify which data (e.g., data type, ranges, categories) to be encrypted. The smartphone may then encrypt the identified data using multiple cryptographic keys, with each key corresponding to a data node or data element in a multi-node data storage structure that represents the health data, and generate unique data identifiers corresponding to each data node and data element. The smartphone shares the encrypted data and the unique data identifiers with a cloud-based service provider, which stores the data securely. The smartphone also sends at least one cryptographic key (e.g., the key corresponding to the root node for the health institution) and the unique data identifiers to an EHR system associated with Regional Hospital. When the data is available for viewing by the cardiologist, a link may be placed in a user interface view of an EHR application when viewing the patient's record. The EHR application may be the same application used by the cardiologist to perform all EHR-related tasks (e.g., entering notes, writing prescriptions, viewing health records). By selecting the link, the EHR application sends a query to the cloud-based service provider to request the health data identified by the unique data identifiers. In response, the cloud-based service provider sends the corresponding data to the EHR application and the EHR application uses the root cryptographic key to decrypt the root node, which enables the EHR application to access the unique identifiers and cryptographic keys to and decrypt the remaining nodes and view the relevant information.

Turning now to the figures, FIG. 1 illustrates a block diagram 102 and a flowchart showing a process 100 for sharing health data from user devices with electronic health record systems, according to at least one example. The diagram 102 includes a service provider 104, which is any suitable combination of computing devices such as one or more server computers, which may include virtual resources, capable of performing the functions described with respect to the service provider 104. For example, the service provider 104 may include one or more different servers and/or services dedicated to handling different aspects of sharing health data. Generally, the service provider 104 is configured to facilitate one-directional sharing of health data, e.g., from a user device 106 to an electronic health record (EHR) system 108. In some examples, the service provider 104 may enable two-directional sharing and/or one-directional from the EHR system 108 to the user device 106.

The diagram 102 also includes the user device 106, which is any suitable electronic user device capable of communicating with other electronic devices over a network such as the Internet, a cellular network, or any other suitable network. In some examples, the user device 106 may be a smartphone or other user device on which specialized applications can operate (e.g., a health application). The user device 106 is associated with or otherwise operated by a user 110. The user 110 is an example of a patient whose health data is the subject of this specification. The user device 106 may include a health data application used to download health data, augment and/or process health data, and share health data (the subject of this specification).

The diagram 102 also includes the EHR system 108. The EHR system 108 is associated with at least one health institution and used to manage electronic health record data from the institution. In some examples, a single EHR system 108 is associated with multiple health institutions and used to manage electronic health record data from the multiple institutions. In particular, the EHR system 108 may store, organize, and/or otherwise manage health record data generated by medical professionals of the health institutions. The EHR system 108 may include one or more gateways, each including one or more endpoints to enable multiple connections between the EHR system 108 and other electronic devices. In some examples, user devices such as the user device 106 may interact with the EHR system 108 using any suitable interfaces such as gateway application programming interfaces (API) or via patient portals including graphical user interfaces. The gateway APIs may define a set of function calls for communications between the EHR system 108 and the user device 106.

FIGS. 1 and 9-12 illustrate example flow diagrams showing processes 100, 900, 1000, 1100, and 1200, according to at least a few examples. These processes, and any other processes described herein, are illustrated as logical flow diagrams, each operation of which represents a sequence of operations that can be implemented in hardware, computer instructions, or a combination thereof. In the context of computer instructions, the operations may represent computer-executable instructions stored on one or more non-transitory computer-readable storage media that, when executed by one or more processors, perform the recited operations. Generally, computer-executable instructions include routines, programs, objects, components, data structures, and the like that perform particular functions or implement particular data types. The order in which the operations are described is not intended to be construed as a limitation, and any number of the described operations can be combined in any order and/or in parallel to implement the processes.

Additionally, some, any, or all of the processes described herein may be performed under the control of one or more computer systems configured with specific executable instructions and may be implemented as code (e.g., executable instructions, one or more computer programs, or one or more applications) executing collectively on one or more processors, by hardware, or combinations thereof. As noted above, the code may be stored on a non-transitory computer-readable storage medium, for example, in the form of a computer program including a plurality of instructions executable by one or more processors.

The process 100 begins at block 112 by the user device 106 storing health data 116 on the user device 106 according to a multi-node data storage structure 114. Examples of the multi-node data storage structure 114 will be described with reference to FIGS. 6-8. Examples of the health data 116 may include clinical health records (e.g., obtained from endpoints of the EHR system 108 and/or a different EHR system), data generated by the user device 106 (e.g., sensor data from sensors of the user device 106, algorithms on the user device 106 may process health data to organize the data, make predictions and/or suggestions), data obtained from accessory devices (e.g., wearable monitoring devices may share sensor health data such as heart rate data or respiratory data with the user device 106), and any other suitable health data.

In some examples, all of the health data 116 may be stored on the user device 106 using the multi-node data storage structure 114. In some examples, only a portion of the health data 116 may be stored using the multi-node data storage structure 114. For example, the health data 116 available for sharing using the techniques described herein may be less than all of the health data stored on the user device 106, e.g., medication data may be available for sharing, but certain wave form data such as electrocardiogram data may be unavailable for sharing. In some examples, the user device 106 may store the health data 116 according to the multi-node data storage structure 114 at least when triggered (e.g., when the user 110 requests sharing using the user device 106, when a request for sharing is received from the EHR system 108, when data that is available to be shared is collected and/or received such as when heart rate data recorded on a smartwatch is shared with the user device 106, and in any other suitable manner). In some examples, prior to storing the health data 116 according to the multi-node data storage structure 114, the user device 106 may query the health data 116 based on a set of defined queries in a configuration file of the user device 106. Such querying may be useful to identify and retrieve specific portions of the health data stored by the user device 106. These portions may correspond to a curated data set that is predefined in the configuration file, derived from a user profile, predicted using a machine-learning technique, or obtained in any other suitable manner.

At block 118, the process 100 includes the user device 106 encrypting the health data 116 using one or more cryptographic keys 120(*a*)-120(N). For example, this may include encrypting each node of the multi-node data storage structure 114 with a unique cryptographic key 120, encrypting each data element in each node with a unique cryptographic key 120, or encrypting each data type and/or data category in each node with a unique cryptographic key 120. In some examples, the user device 106 also uses the cryptographic keys 120 to create a set of unique data identifiers 122(*a*)-122(N). For example, a hashing algorithm may take as input health data 116 and a corresponding cryptographic key 120 to create a unique data identifier 122 that represents the input health data 116. In some examples, generating the unique data identifier 122 may include using a SHA hash algorithm (e.g., SHA-256) or any other suitable hash algorithm to generate a hash of the data stored at the node (e.g., the input health data 116) identified by the unique data identifier 122. In some examples, the number of unique data identifiers 122 in the multi-node data storage structure 114 is equal to the number of cryptographic keys 120. At block 124, the process 100 includes the user device 106 sending encrypted health data 126 and the corresponding unique data identifiers 122(*a*)-122(N) to the service provider 104. In some examples, this may include the user device using a predefined method call to send the encrypted health data 126. The encrypted health data 126 and the unique data identifier 122(*a*)-122(N) may be captured in the multi-node data storage structure 114. Thus, in some examples, the block 124 includes sending the multi-node data storage structure 114, including the health data 126 to the service provider 104. The service provider 104 may be operated by an entity separate from the entity that operates the EHR system 108. In some examples, the service provider 104 is operated by the same entity that provides the platform according to which the user devices 106 operates.

At block 128, the process 100 includes the user device 106 receiving a selection of a health institution to receive at least a portion of the health data 116. In some examples, this may include the user 110 using a user interface at the user device 106 to select the health institution from a pre-populated list of health institutions, to select the health institution after searching for the health institution in a database of available health institutions, and to select in any other suitable manner. In some examples, the user interface of the user device 106 enables selection of data for sharing at a level of granularity lower than all health data or all health data from one institution. For example, the user 110 may select which categories of data to share, which data types of data to share, date ranges to share for which categories and/or data types, and the like.

At block 130, the process 100 includes the user device 106 sending a cryptographic key (e.g., 120(*a*)) and a set of unique data identifiers (e.g., 122(*a*)-122(N)) to the EHR system 108 associated with the health institution. As described elsewhere herein, the EHR system 108 may be configured to use the set of unique data identifiers 122 to query the service provider 104 for portions of the encrypted health data 126. When the encrypted health data 126 is received by the EHR system 108, the EHR system 108 may use the cryptographic key 120 to decrypt the encrypted health data 126. In some examples, the user device 106 sends only one unique data identifier 122 (e.g., an identifier of a root node).

Figure 2:
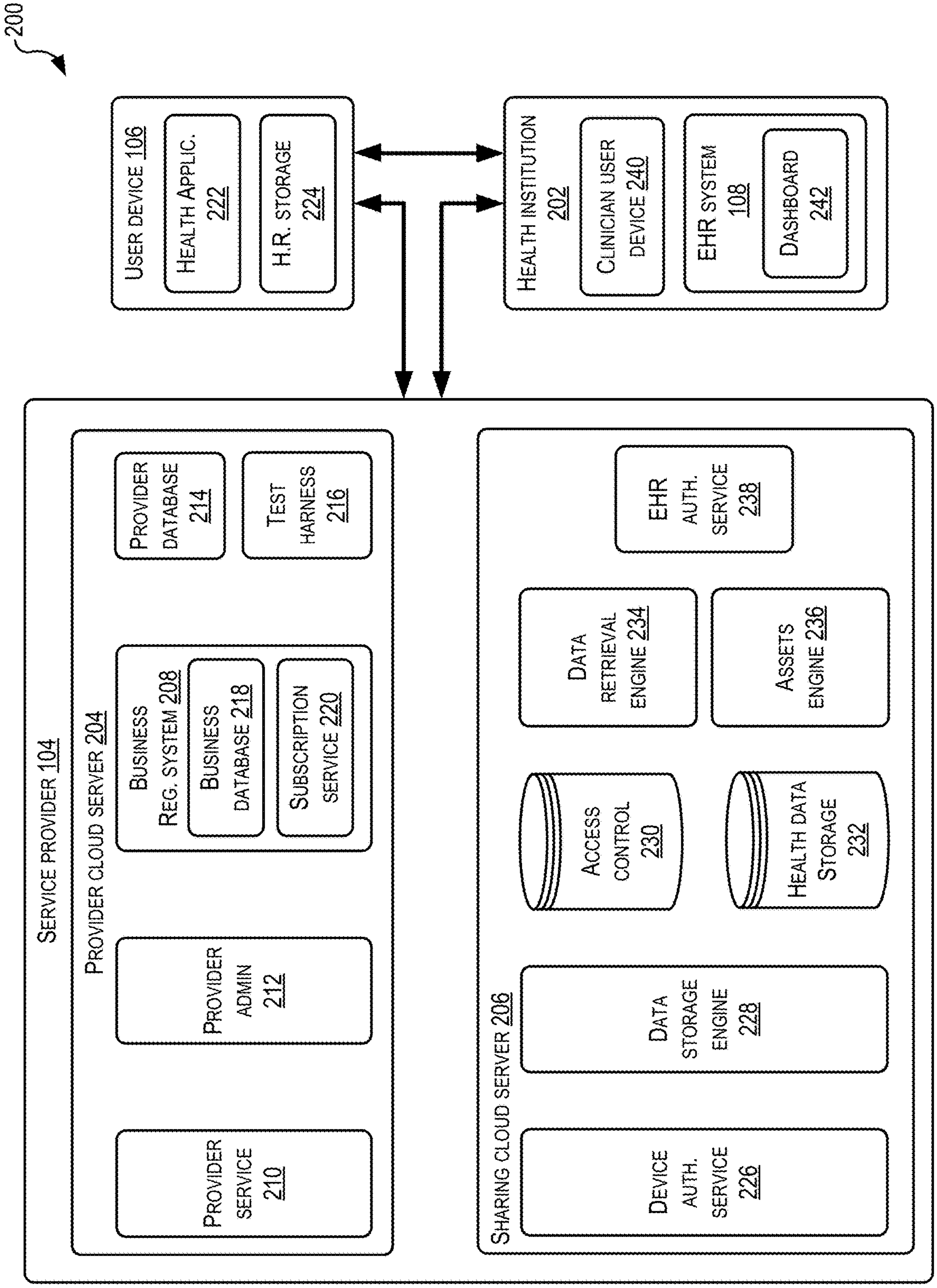
FIG. 2 illustrates a block diagram showing an example architecture or system for enabling sharing of health data from user devices with electronic health record systems, according to at least one example.

FIG. 2 illustrates a block diagram showing an example architecture or system 200 for enabling sharing of health data from user devices with electronic health record systems, according to at least one example. The system 200 includes a few elements introduced in FIG. 1. In particular, the system 200 includes the service provider 104, the user device 106 (e.g., one or any other suitable number of user devices), and the EHR system 108 (e.g., one or any other suitable number of EHR systems) associated with a health institution 202. As appropriate and as illustrated by the arrows, the elements of the system 200 may be communicatively coupled via one or more suitable communication networks. For example, the service provider 104, the user device 106, and the EHR system 108 may be configured to communicate with each other via one or more networks, as described herein and is known in the art.

Beginning with the service provider 104, the service provider 104 includes a provider cloud server 204 and a sharing cloud server 206. Generally, the provider cloud server 204 includes one or more server computers, which may be virtual, and is configured to onboard health institutions to enable sharing of health data, manage registrations of the health institutions once onboarded, and conduct tests of endpoints of the EHR systems 108 of the health institutions 202 to ensure correct operation with the sharing system provided by the service provider 104. Generally, the sharing cloud server 206 includes one or more server computers, which may be virtual, and is configured to manage sharing of health data according to the examples described herein. In particular, different elements of the sharing cloud server 206 manage different aspects of sharing including authorization of user devices 106 and EHR systems 108, data retrieval, and the like.

The provider cloud server 204 includes a business registration system 208, a provider service 210, a provider admin 212, a provider database 214, and a test harness 216. Business registration system 208 may be any suitable collection of hardware and software components configured to collect, store, update, and otherwise manage business locations including those of the health institutions 202. For example, the business registration system 208 may include a business database 218 and a subscription service 220 to enable subscription of the EHR systems 108 of the health institutions 202. When a health institution 202 is subscribed and active, the user devices 106 may be allowed to share health data with the EHR system 108 and connect to and download health record data from the EHR system 108 (e.g., a gateway of the EHR system 108).

As part of subscribing and managing subscriptions, the subscription service 220 may include functionality to collect, store, update, and otherwise manage business locations. In some examples, the subscription service 220 provides one or more user interfaces by which authorized users of the health institution 202 may input information about their location. This information may include geographic information (e.g., a physical address and pin on a map), image information (e.g., logos), contact information (e.g., business, legal, technical), and any other information relating to a business. The subscription service 220 may also be configured to create and/or update record entries in the business database 218 based on information received. For example, an authorized user associated with the health institution 202 may share business information with the subscription service 220. Once this information has been shared and validated, the business information may published for public consumption (e.g., indexed for searching, made available on a map platform, shared directly with users).

The business database 218 may maintain the collected business information and any relationships between entities represented by the business information. In some examples, the business registration system 208 may be used to register other business entities (not just health institutions 202). Records for the health institutions 202 may be maintained in both the business database 218 and a provider database 214 maintained by the provider cloud server system 204. In some examples, the business registration system 208 shares business information with the provider sharing cloud server 206 in any suitable manner.

Turning now to the provider service 210. Generally, the provider service 210 may validate the EHR systems 108, maintain information about the health institutions 202 and associated EHR systems 108, enable searching of the health institutions 202 associated with the EHR systems 108, and manage access of the user devices 106 to the EHR systems 108. The provider cloud server 204 may be implemented in the "cloud." The provider service 210 may also maintain information about the health institutions 202 and associated EHR systems 108 in the provider database 214, enable searching of the health institutions 202 associated with the EHR systems 108, and manage access of the user devices 106 to the EHR systems 108. In some examples, the user devices 106 sends requests to search for the health institutions 202 to the provider service 210. The provider service 210 processes these requests and returns results. In some examples, as part of establishing a connection with one of the EHR systems 108, the user device 106 will check in with the provider service 210 to determine whether any configuration information associated with the EHR system 108 has changed. The configuration information, which may be stored in the provider database 214, may include API information, provider identifiers, status indicator information, and any other suitable information relating to the configuration of the EHR system 108 and/or other entities associated with the EHR system 108.

As part of subscribing a health institution 202, the test harness 216 may be used to test and/or otherwise validate that a test user using a test user device 106 can connect to and download data from the EHR system 108. In this manner, the test harness 216 may simulate actions that one of the user devices 106 may perform to connect to the EHR system 108. In some examples, the test harness 216 may test this connection when a health institution 202 is first subscribed and at other times after the initial subscription. For example, the connection may be tested periodically, when certain conditions are fulfilled, and under any other circumstance. If the test is positive, a status indicator(s) in the provider database 214 associated with the health institution 202, the EHR system 108, and/or a gateway associated with the EHR system 108 may be updated to reflect that the EHR system 108 or the gateway is/are active. If the test is negative, the status indicator(s) may be updated to reflect that the EHR system 108 is inactive. When active, the user devices 106 may be capable of connecting to the gateways of the EHR systems 108. When inactive, the user devices 106 may be unable to connect to the gateways of the EHR systems 108.

The provider admin 212 may generally be used by an administrator or other authorized user to manage aspects of the provider cloud server 204.

The user device 106 may include a health application 222 and a health record storage 224. Generally, the user devices 106 may be associated with and operated by different users (e.g., patients of the health institutions 202). Functionally, the health application 222 may enable the user devices 106 to communicate with the provider cloud server 204 (e.g., to search for the health institutions 202, obtain configuration information about the health institutions 202, and perform other techniques), communicate with the EHR systems 108 of the health institutions 202 (e.g., to download data packages including electronic health records and/or updates to electronic health records and to perform other such techniques), and communicate with the sharing cloud server 206 to upload encrypted health data and perform other techniques described herein.

The sharing cloud server 206 may include a device authentication service 226, a data storage engine 228, an access control storage 230, a health data storage 232, a data retrieval engine 234, an assets engine 236, and an EHR authentication service 238. Generally, the device authentication service 226 is used to authenticate users of the user devices 106 for accessing the service provider 104 and/or the EHR system 108. For example, the device authentication service 226 may use a two-way authentication or mutual authentication such as internet key exchange (IKE), secure shell (SSH), or transport layer security (TLS). In an example that uses TLS, a client-side X.509 certificate may be used to authenticate the identity of the client (e.g., a user device 106) to the server (e.g., the provider sharing cloud sever 206), and an X.509 certificate may be used to authenticate the server to the client. In some examples, the mutual authentication may include the use of usernames and passwords in addition to or instead of certificates. In some examples, the access control storage 230 may store credential data useable by the device authentication service 226.

The data storage engine 228 may be configured to receive encrypted health data from the user device 106 and store it in the health data storage 232. For example, the data storage engine 228 may include a set of method calls to communicate with the user device 106 and store the encrypted health data. The encrypted health data may be passed to the health data storage 232 using a Blob application programming interface (API) to push data to the health data storage.

The access control storage 230 generally stores credentials for health institutions and/or providers. Information in the access control storage 230 may be accessed by the provider admin 212 as part of when an EHR system 108 makes a request for health data storage 232.

As introduced herein, the health data storage 232 may be used to store encrypted health data obtained from the user device 106. The data retrieval engine 234 may be used to retrieve the encrypted health data from the health data storage 232 responsive to requests from a clinician user device 240 (e.g., an example of the user device 106) providing a dashboard 242. For example, the data retrieval engine 234 may use a Blob API to pull data from the health data storage 232.

The assets engine 236 is configured to manage assets of the sharing cloud server 206. This may include removing or otherwise deleting old or stale data in the health data storage 232. In some examples, such deletion may be part of a garbage collection routine, or may be requested or otherwise instructed by the user device 106. For example, the user device may change the way the health data is stored and the assets engine 236 may make the adjustments in the health data storage 232.

The EHR authentication service 238 is used to authenticate the clinician user device 240 and/or the dashboard 242. For example, the EHR authentication service 238 may use a decentralized authentication protocol such as OpenID to authenticate the clinician user device 240 and/or the dashboard.

As introduced herein, the clinician user device 240 may be operated by a clinician or other authorized user to access the health data of the user. The dashboard 242, which may be presented by the clinician user device 240, may be an application such as web application accessible via a web browser of the clinician user device 240 or any other suitable application accessible by the clinician user device 240. In some examples, the dashboard 242 may be hosted by the EHR system 108 and may be the typical dashboard 242 used by the clinician to access electronic health records stored by the EHR system 108. To enable the dashboard 242 to view the health data from the service provider 104, as described herein, the dashboard 242 may be slightly modified to include a link, icon, or other graphical element to enable the clinician to see the health data loaded into the EHR using the techniques described herein. In some examples, EHR system 108 communicates with the health application 222 to authenticate the user of the user device 106. Such communications may occur using an existing Health Level Seven International Standard (HL7) such as Fast Healthcare Interoperability Resource (FHIR) standard describing data elements, data formats, and APIs for exchanging electronic health records. In some examples, the open source implementation of the FHIR standard, referred to as SMART on FHIR (Substitute Medical Applications, Reusable Technologies on FHIR), may be appropriate.

The user device 106 may include the health application 222 and the health record storage 224. As described herein, the health application 222 may be used to perform the techniques described herein such as those described with respect to the flow charts. The health record storage 224 may be used to store the health data that is shared, as described herein, and any other health record data.

Figure 3:
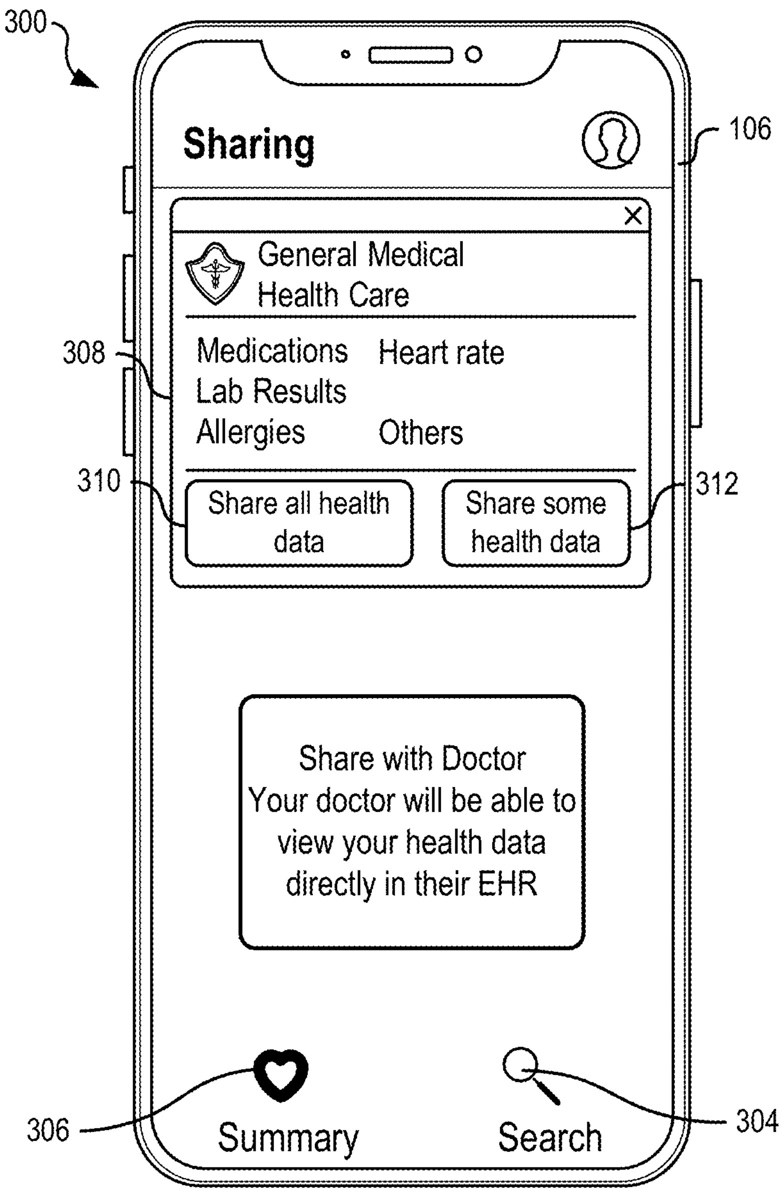
FIG. 3 illustrates a user interface for managing sharing of health data from user devices with electronic health record systems, according to at least one example.

FIG. 3 illustrates a user interface 300 for managing sharing of health data from user devices with electronic health record systems, according to at least one example. The user interface 300 is depicted on a display of the user device 106. Generally, the user interface 300 may be presented within an application on the user device 106, such as a health application. The user interface 300 may include a summary icon 306 used to view a summary of all the health data stored on the user device. For example, within the health application, the user may view and manage all health data on the user device 106, e.g., sensor health data, clinical health data, and any other data. In some examples, the user may search for available providers/health institutions by selecting a search icon 304. This may enable the user to do a keyword search, geographic search, or the like for health institutions that are supported by the service provider 104. In some examples, the user may search the provider database 214 and/or the business database 218.

As depicted, the user interface 300 includes information that identifies a health institution 308 "General Medical Health Care." The health institution 308 may have been located using the search function described with respect to search icon 304. The user interface 300 includes options to share all health data (selection of button 310) and to share some health data (selection of the button 312). Sharing all health data may include all that is available for sharing. Sharing some health data may enable the user to select, e.g., by data type, which data to share. For example, the user may select to share heart rate data but not medication data.

Figure 4:
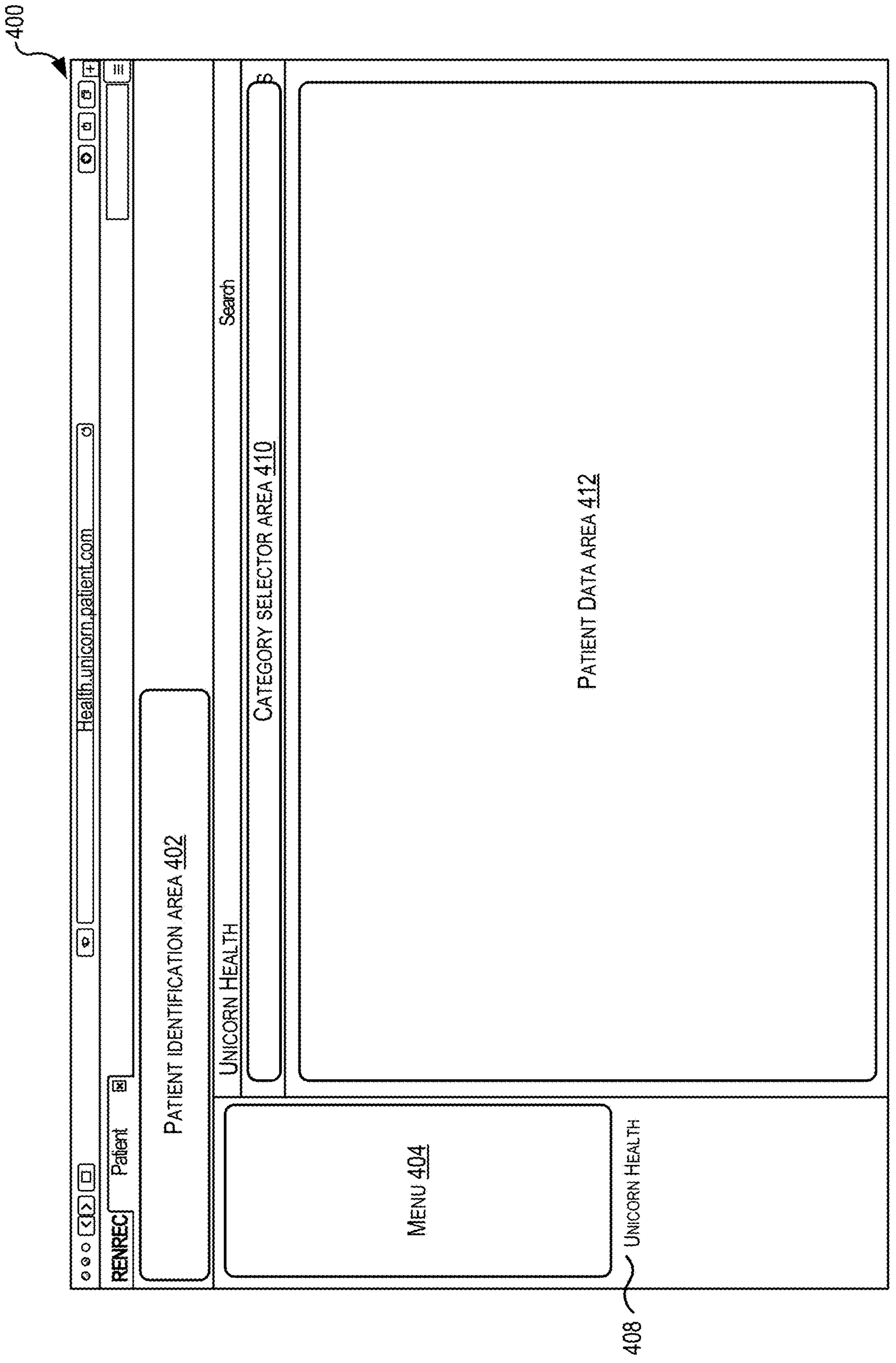
FIG. 4 illustrates a user interface for viewing shared health data, according to at least one example.

FIG. 4 illustrates a user interface 400 for viewing shared health data, according to at least one example. The user interface 400 is depicted on a display of the clinician user device 240 for a clinician who is treating patients. For example, the user interface 400 may be a view in a dashboard and/or web application provided by the EHR system 108. The user interface 400 may be used to view health record data conventionally stored and accessed using the EHR system 108. Thus, the user interface 400 includes a patient identification area 402. The patient identification area 402 includes demographic and identifying information about a patient "Justin Weaver." The user interface 400 also includes a menu 404 for navigating through different views for viewing data and/or performing tasks relating to administering care to the patient. Example views include inpatient summary, patient handoff, orders, medication list, task list, histories, allergies, diagnosis and problems, documents and reports, discharge summary, and patient information. The menu 404 may also include an option for viewing the health data that is the subject of this application. This option is labeled "Unicorn Health."

In the view depicted in FIG. 4, the unicorn health option 408 has been selected. Thus, the user interface 400 may depict a view that includes a category selector area 410 extending across the top of the unicorn health view. Categories in the category selector area 410 represent different categories of data and/or data types that can be viewed using within the Unicorn Health view. For example, these categories may include a view all tab, an activity tab to view activity information (e.g., steps recorded, workout minutes, types of workouts, standing throughout day, and other such information recorded by the user device 106 and/or an accessory device), vitals information (e.g., body temperature, pulse rate, respiration rate, blood pressure), heart information (e.g., heart rate information), respiratory information, audio information (e.g., recordings relating to a health care interaction or any other information to share with the clinician), and condition information.

Selection of one of the categories in the category selector area 410 may cause the information in the patient data area 412 to update, which may include one or more data views. Each data view may correspond to a different data type. For example, a first data view may represent heart rate for some period of time, a second data view may represent step data, a third data view may represent blood pressure, a fourth data view may represent medication data, and a fifth data view may represent a metabolic panel.

Figure 5:
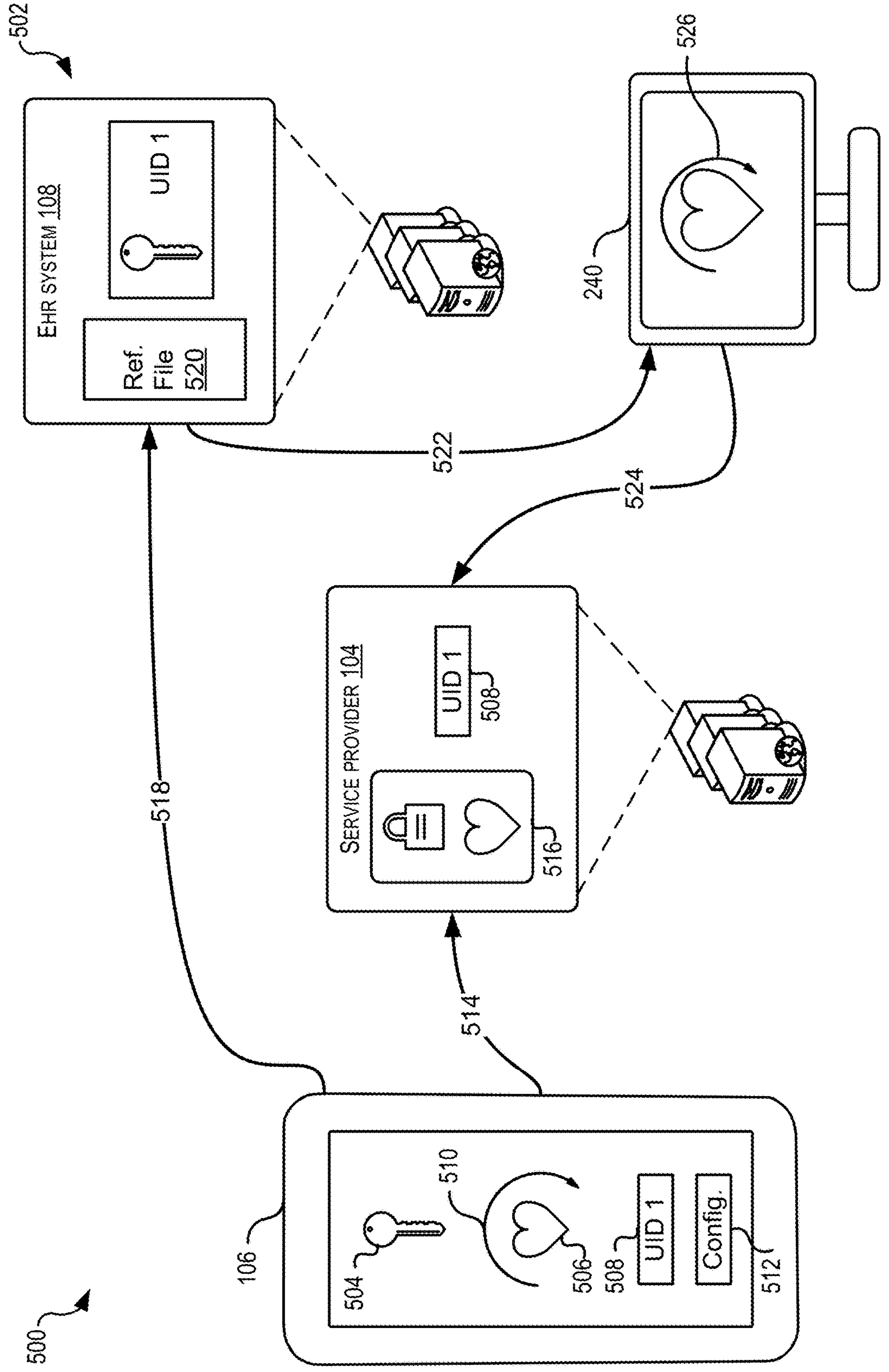
FIG. 5 illustrates a block diagram showing an example system and an example process for sharing health data from user devices with electronic health record systems, according to at least one example.

FIG. 5 illustrates a block diagram showing an example system 502 and an example process 500 for sharing health data from user devices with electronic health record systems, according to at least one example. In particular, FIG. 5 depicts aspects of end-to-end encryption of the data within the system 502. The system 502, which is an example of the system 200, includes the user device 106, the service provider 104, the EHR system 108, and the clinician user device 240, which may include a dashboard presented thereon by an EHR application. FIG. 5 is included to depict graphically the flow of cryptographic key(s) 504 (e.g., the cryptographic keys 120), health data 506 (e.g., the health data 116), and unique data identifiers 508 (e.g., the unique data identifier 122) by and between the elements of the system 502.

The process 500 begins at 510 by the user device 106 accessing a configuration file 512 to determine query information for running a query to identify health data 506, and encrypting the identified data using the cryptographic key 504 (e.g., a symmetric key). The configuration file 512 may define the different data categories, data types, and the like that can be shared using the techniques described herein. When triggered, according to a periodic schedule, or in any other manner, the user device 106 (e.g., the health application) may run a query to identify the relevant data that can be identified, encrypted, and shared. At least some of the health data 506 may be stored in accordance with the multi-node data storage structure. In some examples, once data has been shared with a health institution, the user device 106 may periodically update the data by running a query on the data, identifying differences, and sharing the new data. In some examples, the user device 106 may share all of the data, not just the differences between old and new.

At 514, the process 500 includes the user device 106 uploading the health data 506, now encrypted, and the unique data identifier 508 to the service provider 104. The encrypted health data is identified as 516. The unique data identifier 508 is an Lookup ID for at least one of the data nodes of the multi-node data storage structure (e.g., 114). In some examples, the unique data identifier 508 identifies the root data node of the multi-node data storage structure, which may enable identification of corresponding branch nodes.

In some examples, the process 500, e.g., as part of block 514, may include the service provider 104 anonymously authenticating the user device 106 that uploads the health data 506. Such authentication may include authenticating that the user device 106 is of a type that is approved to upload to the service provider 104 (e.g., a user device from a particular manufacturer, a user device of a particular model, a user device operating a specific operating system, a user device operating a specific version of an operating system, a user device operating a particular application, and any other distinguishing type). For example, the user device 106 may provide an anonymized credential, signature, or other information element that may be used by the service provider to authenticate the user device 106. As described herein, the service provider 104 may store health data 506 in a privacy-protected manner that keeps the service provider 104 from being capable of deriving identities of the users to whom the health data belongs. Thus, the authentication of the user device 106 may be performed in a manner that ensures that the identity of the user operating the user device 106 is withheld from the service provider 104.

In some examples, authenticating the user device 106 to ensure that it is a valid device may include the user device 106 providing a device identifier to the service provider 104 and the service provider 104 checking that the device identifier is on a list of authorized devices. In some examples, authenticating the user device 106 may include the user device 106 providing a token or other such information element to the service provider 104 and the service provider 104 confirming that authenticity of the device 106 using the token.

At 518, the process 500 includes the user device 106 storing/updating a document reference file 520 on the EHR system 108 with the cryptographic key 504 and the unique data identifier 508. In some examples, this information may be sent to the EHR system 108 using one or more APIs provided by the EHR system 108. Once received, the EHR system 108 stores the cryptographic key 504 and unique data identifier 508 in association with each other.

At 522, the process 500 includes the clinician user device 240 retrieving the cryptographic key 504 and unique data identifier 508 from the EHR system 108, e.g., by using the API associated with the document reference file 520 of the EHR system 108. With the cryptographic key 504 and unique data identifier 508, the clinician user device 240, at 524 can retrieve the encrypted data node identified by the unique data identifier 508 by providing the unique data identifier 508 to the service provider 104. In response, the service provider 104 retrieves the data associated with the encrypted data node and sends it back to the clinician user device 240.

In some examples, the clinician user device 240 also provides a token (e.g., OpenID token) or other authentication information for authentication by the service provider 104. In some examples, authentication of the actual clinician who is using the clinician user device 240 may be the responsibility of the EHR system 108 or other internal system that is separate from the service provider 104. In other words, the service provider 104 may authenticate at a health institution level (e.g., confirm that the clinician user device 240 and/or the dashboard belong to a known and trusted health institution), not necessarily at a user level (e.g., that the clinician operating the clinician user device 204 is authorized to view the health data). In conclusion, at 526, the process 500 includes the clinician user device 240 decrypting the health data 506 using the cryptographic key 504.

Figure 6:
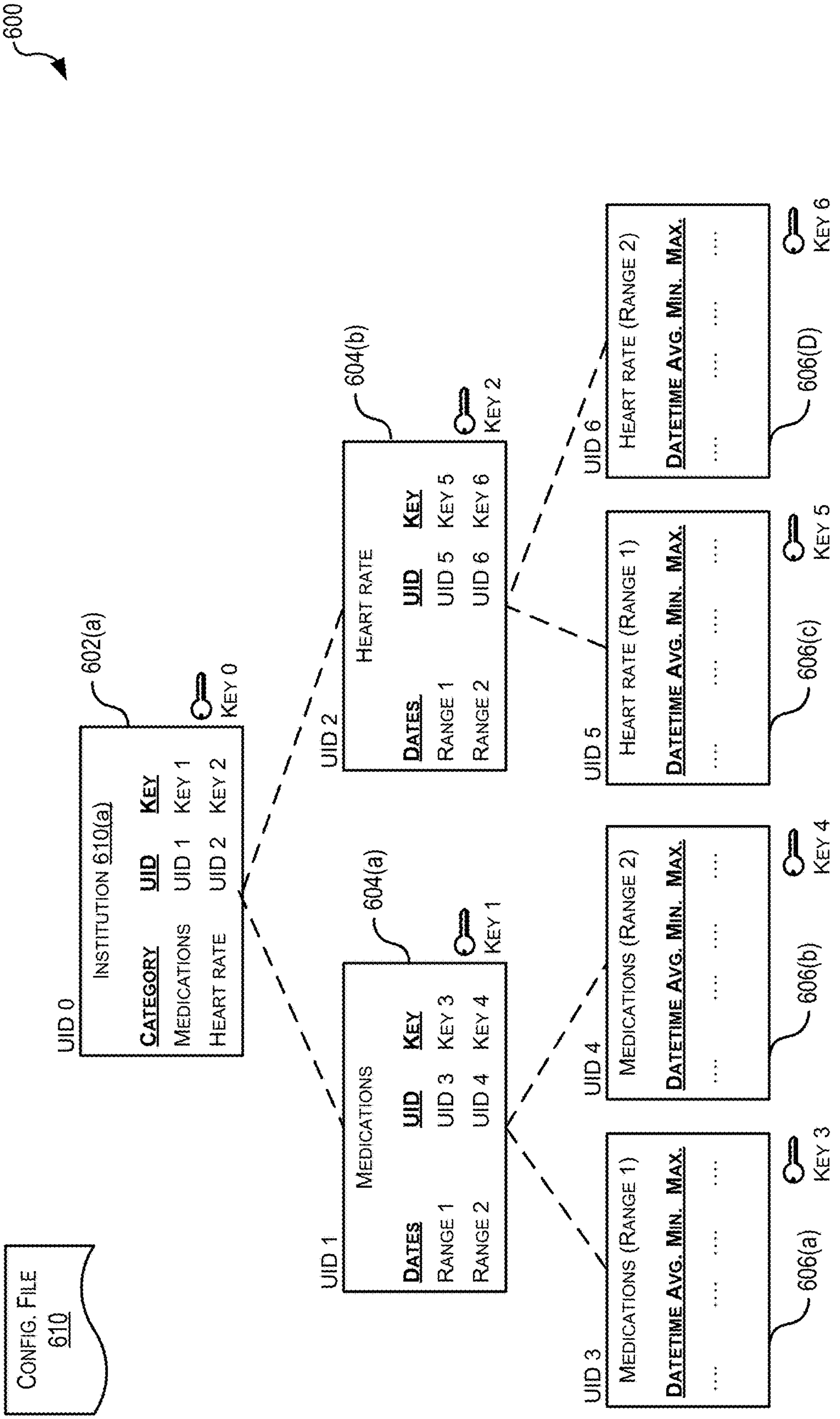
FIG. 6 illustrates a block diagram showing a multi-node data storage structure for storing and sharing health data, according to at least one example.

FIG. 6 illustrates a block diagram showing a multi-node data storage structure 600 for storing and sharing health data from user devices with electronic health record systems, according to at least one example. The multi-node data storage structure 600 is an example of the multi-node data storage structure 114. The multi-node data storage structure 600 includes a plurality of nodes that include an institution node 602(*a*) (e.g., a root node), category nodes 604(*a*) and 606(*b*), and data nodes 608(*a*)-608(*d*). The category nodes 604 and the data nodes 608 may be considered branch nodes.

The institution node 602(*a*) is associated with a health institution 610(*a*). This is the health institution with which the health data has been shared. Thus, in the example from FIG. 3, the health institution would be General Medical Health Care. The institution node 602(*a*) is encrypted with Key 0 and is uniquely identified by unique data identifier UID 0.

The institution node 602(*a*) includes data organized by one or more categories (e.g., medications and heart rate), which correspond directly to the category nodes 604(*a*) and 606(*b*). For each category node 604, the institution node 602(*a*) stores a unique data identifier (e.g., UID 1 and UID 2) and a key (e.g., Key 1 and Key 2). As described in FIG. 5, when a user desires to share the data represented by the multi-node data storage structure 600 with the health institution 610(*a*), key 0 and UID 0 are shared with the health institution. This enables the health institution to identify the institution node 602(*a*) and decrypt the contents of the node to obtain UID 1 and UID 2 and corresponding Keys 1 and 2.

As illustrated, each category node 604 is uniquely identified by its UID and is encrypted with its Key. For example, the category node 604(*a*) is identified by the UID 1 and encrypted with Key 1. The medications category node 604(*a*) identifies one or more data ranges for which data of the data type "Medications" is stored by the multi-node data storage structure 600. For example, the medications category node 604(*a*) identifies data node 606(*a*) (e.g., medication Range 1 identified by UID 3 and encrypted with Key 3) and data node 606(*b*) (e.g., medication Range 2 identified by UID 4 and encrypted with Key 4). The heart rate category node 604(*b*) similarly identifies data ranges for which data of the data type "Heart Rate" is stored by the multi-node data storage structure 600. For example, the heart rate category node 604(*b*) identifies data node 606(*c*) (e.g., heart rate Range 1 identified by UID 5 and encrypted with Key 5) and data node 606(*d*) (e.g., heart rate Range 2 identified by UID 6 and encrypted with Key 6). The data from the data nodes 606 is used to populate the data views in the patient data area 412 in the user interface 400.

Each data node 606 is used to store a sampling range and sampling frequency of data of the corresponding data type. For example, the heart rate Range 1 of data node 606(*c*) may correspond to a month's worth of data sampled weekly. The heart rate Range 2 of the data node 606(*d*) may correspond to a week's worth of data sampled daily or even more frequently. The values for the different ranges may be stored by the data nodes 606. Of course different sampling ranges and sampling frequencies are possible such as, for example, years, months, quarters of years, weeks, days, hours, minutes, seconds. In some examples, the data Ranges are predefined by one or more clinicians, which, in some examples, may correspond to healthcare standard measurements (e.g., it may be standard to view heart rate over a daily period sampled every 30 minutes to identify daily peaks and valleys).

A configuration file 608 (e.g., the configuration file 512) is used to generate the multi-node data storage structure 600. The configuration file 608 may define each medical category to be collected along with different combinations of sampling ranges and sampling frequencies. The user device 106 may reference the configuration file 608 as it collects and encrypts the multi-node data storage structure 600.

To generate the multi-node data storage structure 600, the user device 106 may begin by collecting and syncing data of the data nodes 606. The data nodes 606 and category nodes 604 may be synced with the service provider 104 as soon as they have been generated and/or may be queued and synced at some different frequency. The queues may be defined by size (e.g., as soon as five mb of data is ready, it is sent), by quantity of nodes (e.g., as soon as five nodes are ready, it is sent), or in any other suitable manner. The institution nodes 602(*a*) may be synced after all of the other nodes have been synced.

The multi-node data storage structure 600 graphically represents relationships between nodes, but should not be viewed as limiting. For example, nodes are illustrated as “connected” by dashed lines. While lower nodes (e.g., the root node) do reference higher nodes in the multi-node data storage structure 600, the data structure does not actually maintain associations directly between nodes. Thus, if one node were obtained by a nefarious user, that user would be unable to obtain other nodes.

Figure 7:
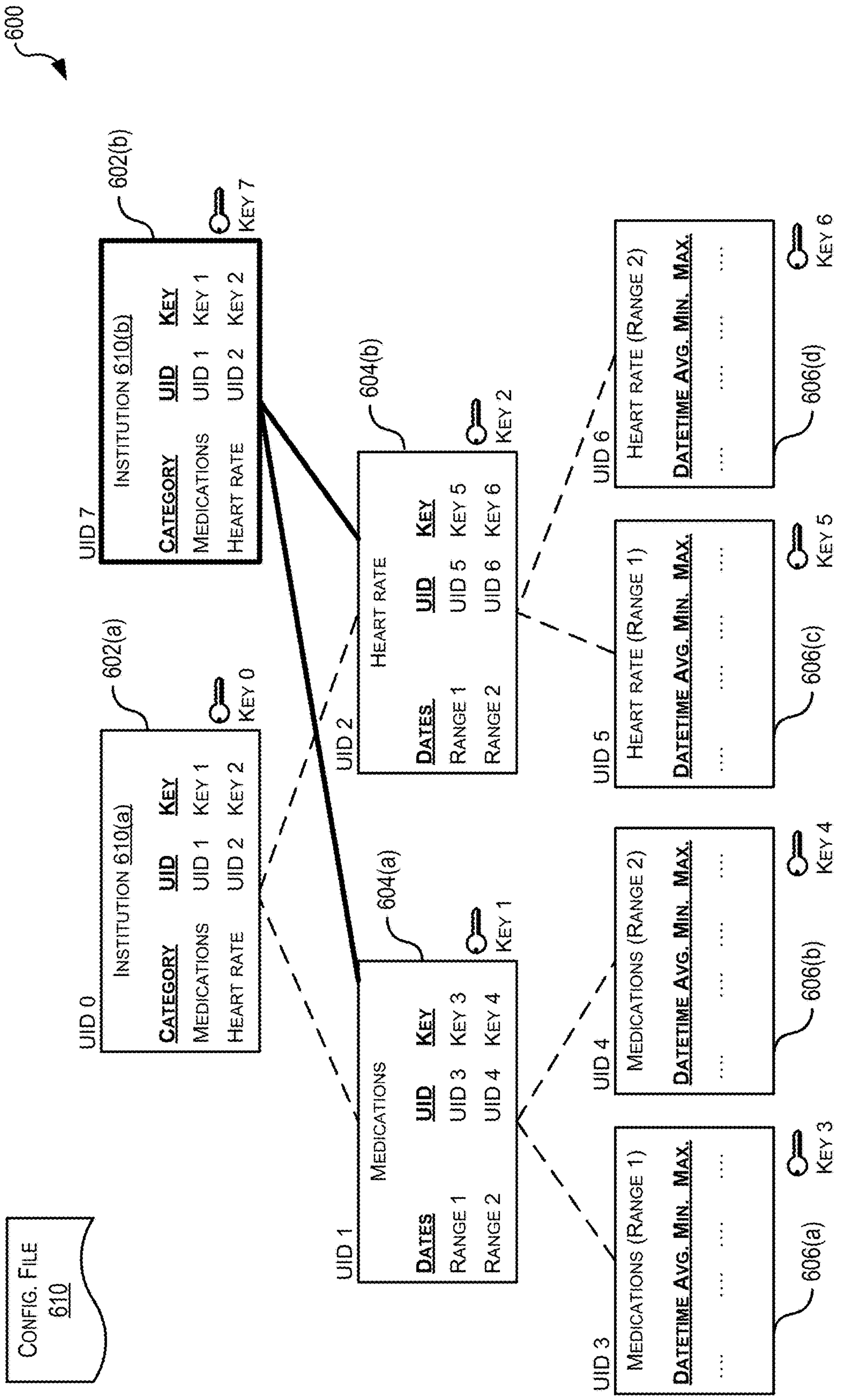
FIG. 7 illustrates a block diagram showing a multi-node data storage structure for storing and sharing health data, according to at least one example.

FIG. 7 illustrates a block diagram showing adding a new sharing institution to the multi-node data storage structure 600, according to at least one example. For example, if the user decided to share their health data with a new health institution, a new institution node 602(*b*) may be created for the new health institution. The new institution node 602(*b*) identifies each category node 604(*a*) and 604(*b*), includes its own unique identifier (e.g., UID7), and is encrypted with its own Key 7. In this example, since the new institution node 602(*b*) includes the key information and the unique identifier information for the category nodes, sharing of the UID 7 and Key 7 with the health institution 610(*b*) enables the health institution to identify and decrypt the institution node 602 (*b*), then the category nodes 604, and then the data nodes 606.

Figure 8:
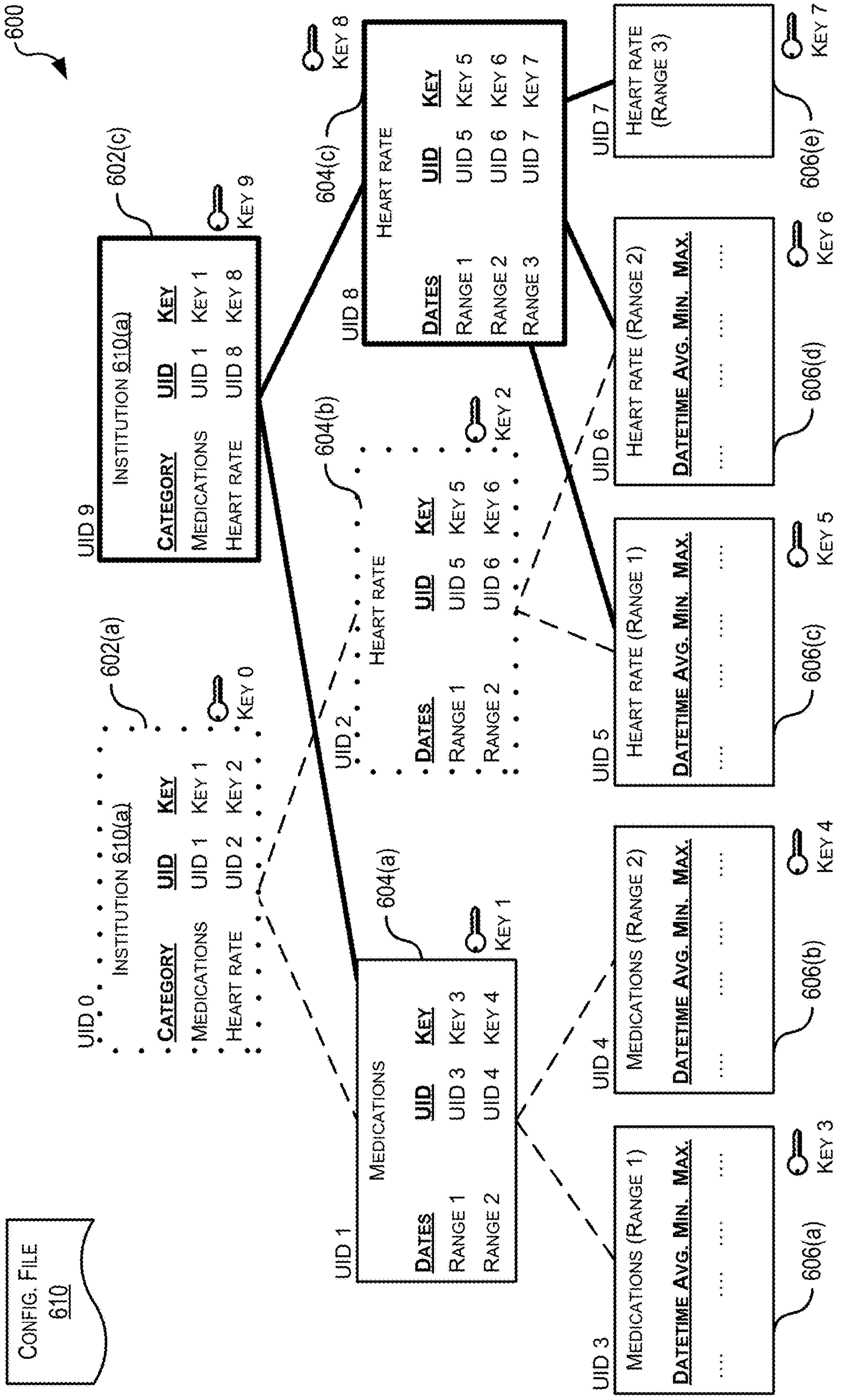
FIG. 8 illustrates a block diagram showing a multi-node data storage structure for storing and sharing health data, according to at least one example.

FIG. 8 illustrates a block diagram showing appending of new data to the multi-node data storage structure 600, according to at least one example. In this example, a new data node 606(*e*) corresponding to a new range of heart rate data is added to the multi-node data storage structure 600. Because of this, a new category node 604(*c*) is generated, which includes the old data node information from the category node 604(*b*) and the data node information from the new data node 606(*c*). Because of this, a new institution node 602(*c*) is generated, which includes the old category node information from the category node 604(*a*) and the new category node information from the new category node 604(*c*). The old institution node 602(*a*) and the old category node 604(*b*) may be deleted from the multi-node data storage structure 600.

Figure 9:
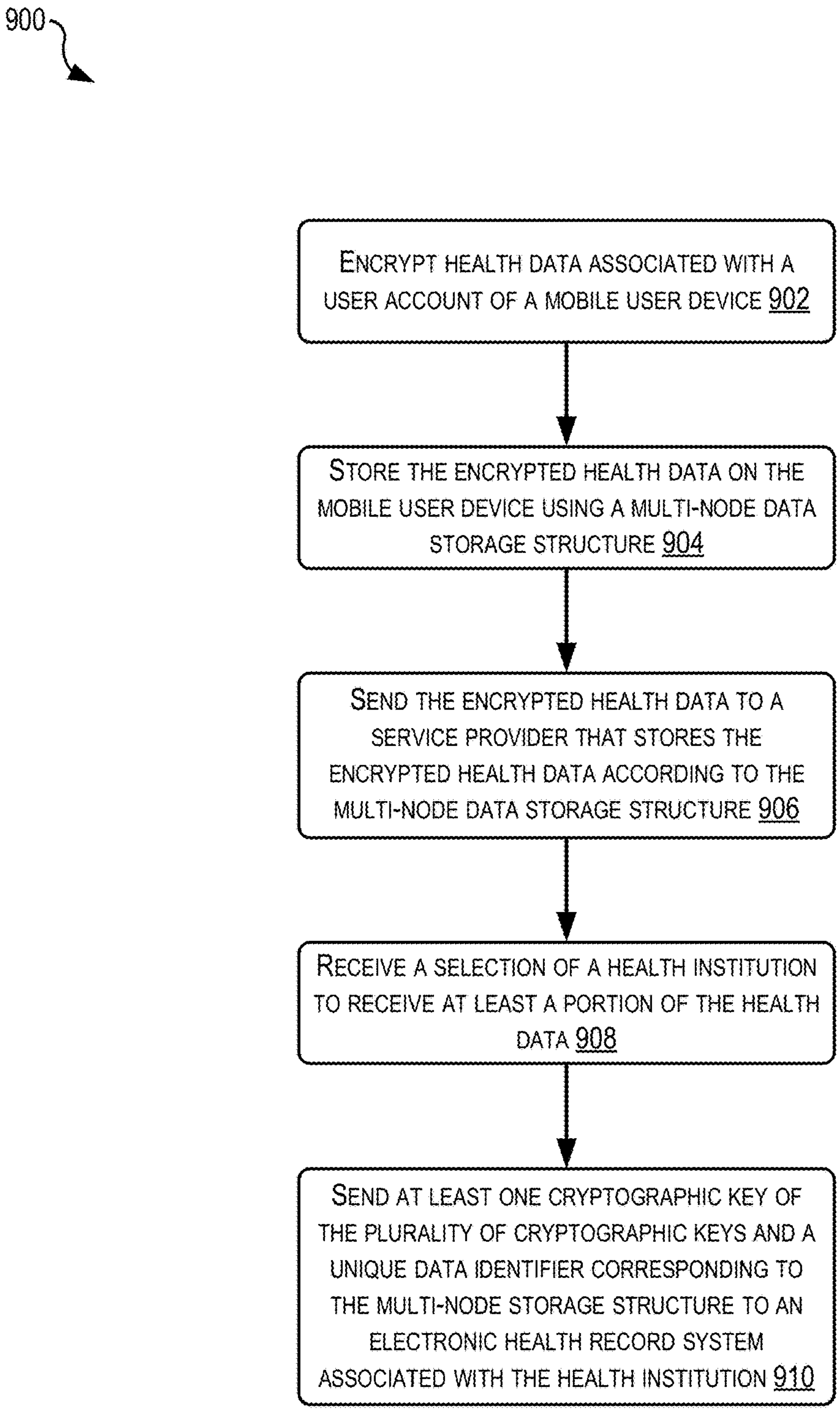
FIG. 9 illustrates a flow chart showing an example process for sharing health data from user devices with electronic health record systems, according to at least one example.

FIG. 9 illustrates a flow chart showing an example process 900 for sharing health data from user devices with electronic health record systems, according to at least one example. The process 900 may be performed by the health application 222 (FIG. 2) of the user device 106 (FIG. 1).

The process 900 begins at block 902 by the user device 106 encrypting health data associated with a user account of the mobile user device. In some examples, encrypting the health data may be performed using a plurality of cryptographic keys. In some examples, encrypting the health data may include encrypting each node of the multi-node storage structure using a unique cryptographic key of the plurality of cryptographic keys.

The health data may include clinical health record data, sensor data, and/or any other suitable type of health data. In some examples, the clinical health record data is received from the electronic health record system or from a different health record system associated with a different health institution. In some examples, the sensor data is generated by a sensor of the mobile user device or received from a different user device (e.g., accessory device such as a watch, wearable monitor) associated with the mobile user device. In some examples, a first portion of the health data is obtained by the mobile user device from the electronic health record system, and a second portion of the health data is obtained by the mobile user device from a different electronic health record system associated with a different health institution. In some examples, the health data is organized into a plurality of categories. In this example, the multi-node data storage structure may include a root node that represents the health institution and a plurality of branch nodes corresponding to each of the plurality of categories.

At block 904, the process 900 includes the user device 106 storing the encrypted health data on the user device 106 using a multi-node data storage structure (e.g., FIG. 6). In this example, each node of the multi-node data structure may be identified by a unique data identifier.

At block 906, the process 900 includes the user device 106 sending the encrypted health data to a service provider that stores the encrypted health data according to the multi-node data storage structure. In this example, the unique data identifier may identify at least one node of the multi-node data storage structure. For example, the unique data identifier may identify an institution node of the multi-node data storage structure.

At block 908, the process 900 includes the user device 106 receiving a selection of a health institution to receive at least a portion of the health data. For example, this may include receiving the selection via a user interface (e.g., FIG. 3) of the user device 106. In some examples, blocks 902-906 are responsive to receiving the selection of the health institution. The selection may represent a request to share the portion of the health data with the health institution.

At block 910, the process 900 includes sending at least one cryptographic key of the plurality of cryptographic keys and a unique data identifier corresponding to the multi-node storage structure to an electronic health record system associated with the health institution, the electronic health record system enabled to use the at least one cryptographic key and the unique data identifier to access and decrypt the portion of the health data from the service provider server. In some examples, the unique data identifier is unique to the health institution.

In some examples, the unique data identifier may be a first unique data identifier of a plurality of unique data identifiers maintained by the mobile user device and corresponding to the multi-node storage structure. In this example, individual unique data identifiers of the plurality of unique data identifiers are associated with at least one of a particular health institution, a particular category of health data, or a predefined data range corresponding to a respective category of health data.

In some examples, individual cryptographic keys of the plurality of cryptographic keys are associated with at least one of a particular health institution, a particular category of health data, or a predefined range corresponding to a respective category of health data.

In some examples, the process 900 may include receiving, as a user input, information identifying a category of the health data, and determining the portion of the health data based at least in part on the category.

Figure 10:
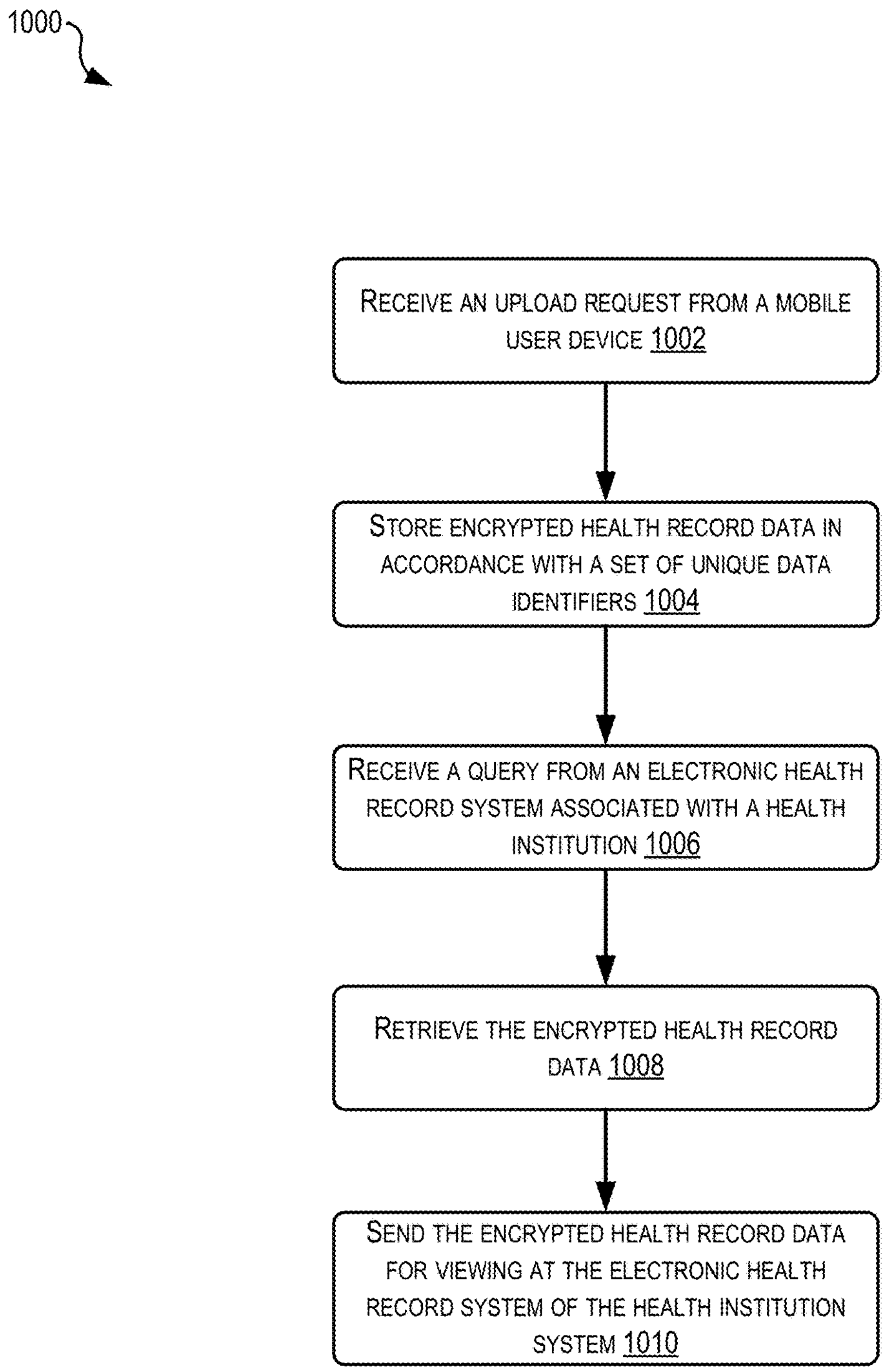
FIG. 10 illustrates a flow chart showing an example process for sharing health data from user devices with electronic health record systems, according to at least one example.

FIG. 10 illustrates a flow chart showing an example process 1000 for sharing health data from user devices with electronic health record systems, according to at least one example. The process 1000 may be performed by the service provider 104 (FIGS. 1 and 2).

The process 1000 begins at block 1002 by the service provider 104 receiving an upload request from a mobile user device. The upload request may include encrypted health record data and a set of unique data identifiers corresponding to the encrypted health record data.

At block 1004, the process 1000 includes the service provider 104 storing the encrypted health record data in accordance with the set of unique data identifiers. This may include storing the encrypted health record data in a secure storage of the service provider 104.

At block 1006, the process 1000 includes the service provider 104 receiving a query from an electronic health record system associated with a health institution. The query may include at least one unique storage identifier of the set of unique data identifiers.

At block 1008, the process 1000 includes the service provider 104 retrieving the encrypted health record data. The query may also include a cryptographic key used to encrypt at least a portion of the encrypted health record data. For example, the cryptographic key may correspond to an institution node of a multi-node data storage structure, with the institution node representing the health institution.

At block 1010, the process 1000 includes the service provider 104 sending the encrypted health record data for viewing at the electronic health record system of the health institution system. This may include sending the health record data for viewing at a dashboard of a clinician user device, as described herein in FIG. 4. In some examples, sending the encrypted health record data for viewing at the electronic health record system may include sending the encrypted health record data without sending cryptographic keys for decrypting the encrypted health record data. The cryptographic keys may have been used to originally encrypt the health record data (e.g., by the user device 106) before it was synced with the service provider 104.

Figure 11:
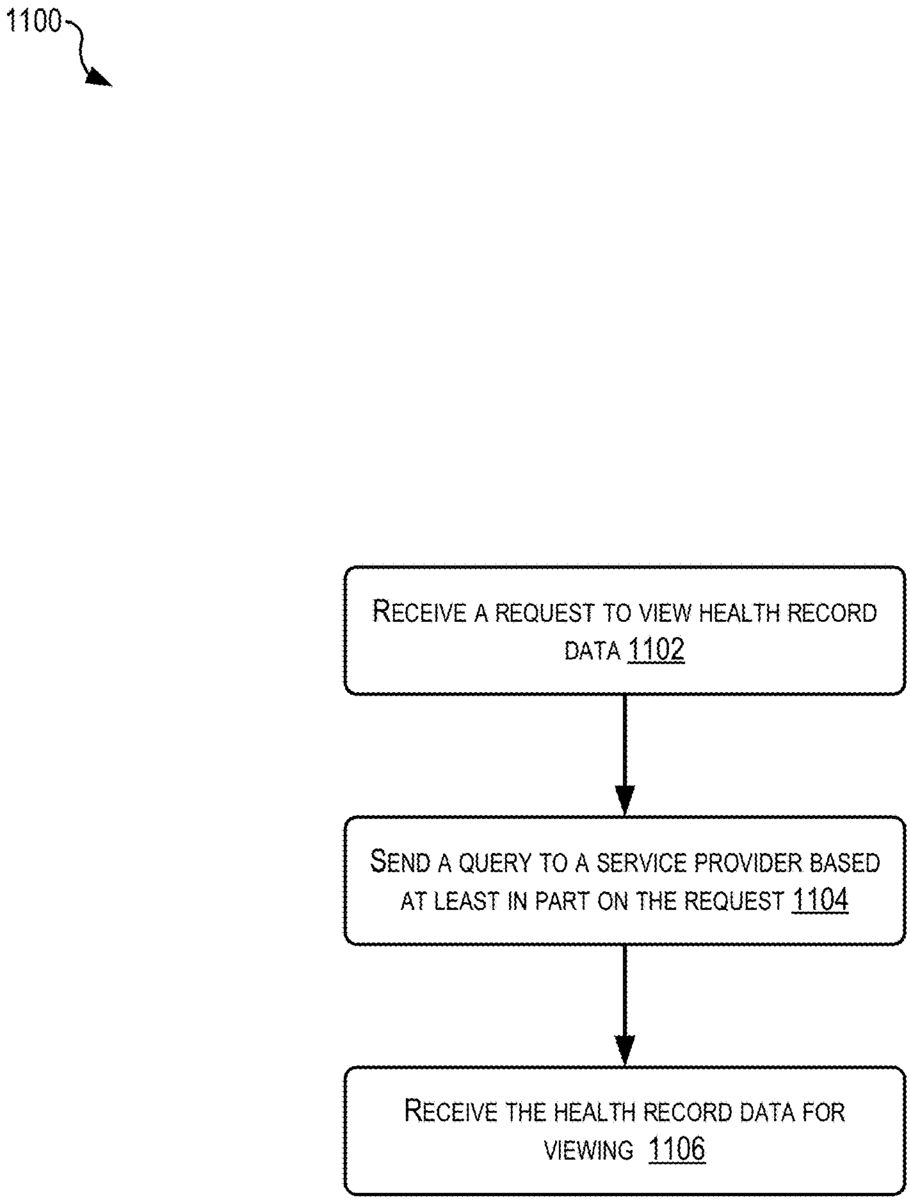
FIG. 11 illustrates a flow chart showing an example process for viewing health record data using a dashboard and/or application of a clinician user device, according to at least one example.

FIG. 11 illustrates a flow chart showing an example process 1100 for viewing health record data using an dashboard and/or application of a clinician user device, according to at least one example. The process 1100 may be performed by the dashboard 242 (FIG. 2) of the EHR system 108 (FIG. 1), as executed by the clinician user device 240 (FIG. 2).

The process 1100 begins at block 1102 by the dashboard 242 receiving a request to view health record data. For example, a clinician may access a user interface such as the user interface 400 to view health record data of a patient. The request may be received via the user interface 400.

At block 1104, the process 1100 includes the dashboard 242 sending a query to a service provider (e.g., the service provider 104) based at least in part on the request. The query may include a unique data identifier that is specific to the health institution. The unique data identifier may identify a node of the multi-node data storage structure that is specific to the patient.

At block 1106, the process 1100 includes the dashboard 242 receiving the health record data for viewing. The health record data may be received within the dashboard in a manner such that the data is stored in memory of the clinician user device 240 and not persisted after the viewing session ends. In this manner, the patient's data is protected.

Figure 12:
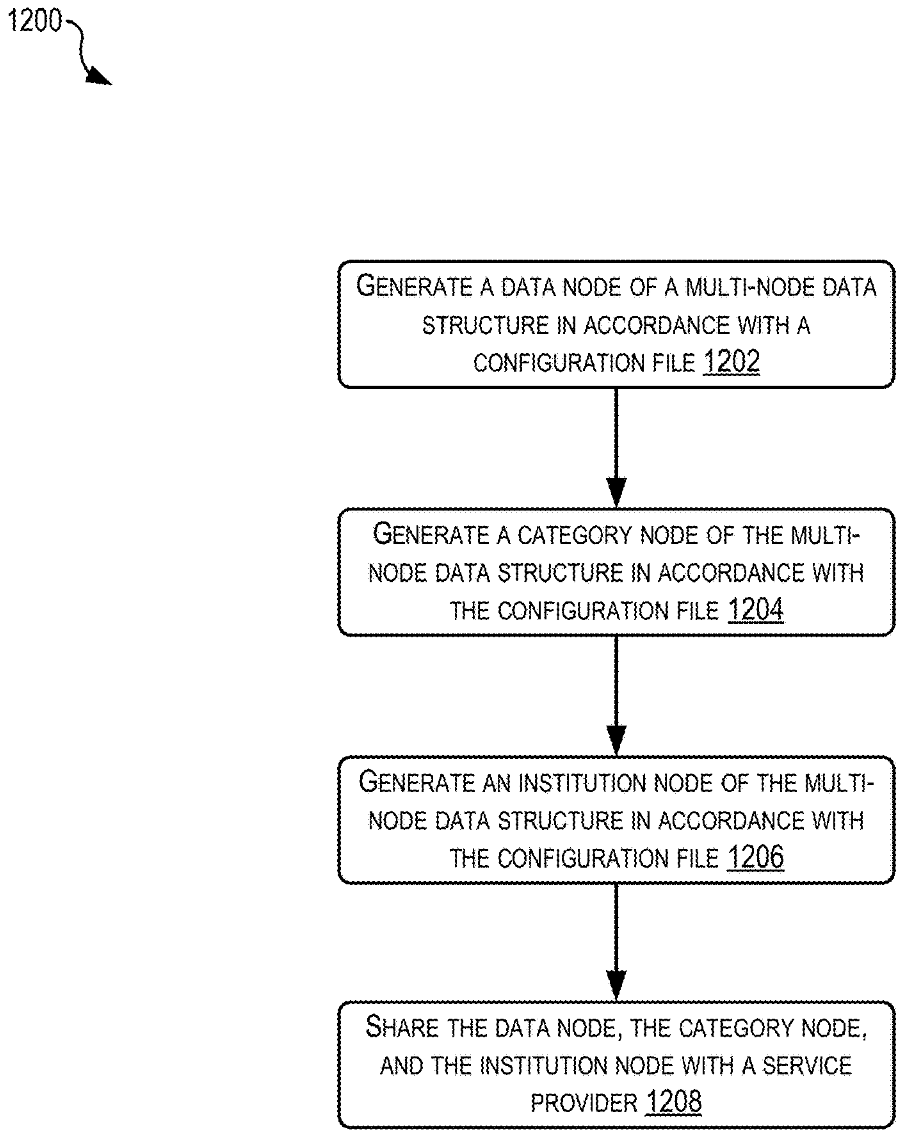
FIG. 12 illustrates a flow chart showing an example process for generating a multi-mode data storage structure for storing and sharing health data, according to at least one example.

FIG. 12 illustrates a flow chart showing an example process 1200 for generating a multi-mode data storage structure for storing and sharing health data, according to at least one example. The process 1200 may be performed by the health application 222 (FIG. 2) of the user device 106 (FIG. 1).

The process 1200 begins at block 1202 by the user device 106 generating a data node of a multi-node data storage structure in accordance with a configuration file. The multi-node data storage structure is an example of the multi-node data storage structure 600 and the configuration file is an example of the configuration file 608. The data node may be a first unique data identifier and encrypted using a first cryptographic key. In some examples, the multi-node data structure is usable for other systems to query health data represented by the multi-node.

At block 1204, the process 1200 includes the user device 106 generating a category node of the multi-node data structure in accordance with the configuration file. The category node may include the first unique data identifier and the first cryptographic key. The category node may be identified by a second unique data identifier and encrypted using a second cryptographic key.

At block 1206, the process 1200 includes the user device 106 generating an institution node of the multi-node data structure in accordance with the configuration file. The institution node may include the second unique data identifier and the second cryptographic key. The institution node may be identified by a third unique data identifier and encrypted using a third cryptographic key.

At block 1208, the process 1200 includes the user device 106 sharing the data node, the category node, and the institution node with a service provider.

In some examples, the process 1200 may further include the user device 106 dynamically generating a set of queries based at least in part on the configuration file. In this example, generating the data node in accordance with the configuration file may include executing at least one query of the set of queries to collect a set of health data to populate the data node. The configuration file may identify one or more required ranges corresponding to the set of health data.

In some examples, the process 1200 may further include the user device 106 determining that each of generating the data node, generating the category node, and generating the institution node was successful. In this example, the process 1200 may further include the user device 106, after determining that generating the data nodes, generating the category node, and generating the institution node was successful, sending the third unique data identifier and the third cryptographic key to an electronic health record system associated with a health institution. The third cryptographic key and the third unique data identifier may correspond to the institution node that represents data shared with the health institution.

In some examples, the process 1200 may further include receiving a request to share health data with a health institution responsive to the request, sending the third unique data identifier and the third cryptographic key to an electronic health record system associated with the health institution. In some examples, sending the third unique data identifier and the third cryptographic key to the electronic health record system may include sending without including other unique data identifiers or other cryptographic keys. In some examples, the third unique data identifier may include a hash that represents data of the institution node, including the second unique data identifier and the second cryptographic key. In some examples, the process 1200 may further include generating the third unique data identifier by hashing data representing the second unique data identifier and the second cryptographic key.

In some examples, the institution node may be a first institution node. In this example, the process 1200 may include generating a second institution node of the multi-node data structure in accordance with the configuration file. The second institution node may include the second unique date identifier and the second cryptographic key. The second institution node may be identified by a fourth unique identifier and encrypted using a fourth cryptographic key.

In some examples, the institution node may be a first institution node, the category node may be a first category node, and the data node may be a first data node. In this example, the process 1200 may include generating a second data node of the multi-node data structure in accordance with the configuration file. The second data node may be identified by a fourth unique identifier and encrypted using a fourth cryptographic key. The process 1200 may further include generating a second category node of the multi-node data structure in accordance with the configuration file. The second category node may include: (i) the first unique data identifier; (ii) the first cryptographic key; (iii) the fourth unique identifier; and (iv) the fourth cryptographic key. The second category node may be identified by a fifth data identifier and encrypted using a fifth cryptographic key. The process 1200 may further include generating a second institution node of the multi-node data structure in accordance with the configuration file. The second institution node may include: (i) the second unique data identifier; (ii) the second cryptographic key; (iii) the fifth data identifier; and (iv) the fifth cryptographic key. The second institution node may be identified by a sixth unique data identifier and encrypted using a sixth cryptographic key.

In some examples, the process 1200 may further include deleting the first institution node and the first category node. In some examples, the process 1200 may further include sending a deletion request to the service provider to delete the first institution node and the first category node from storage of the service provider.

In some examples, sharing the data node, the category node, and the institution node with the service provider may include syncing the data node, the category node, and the institution node with the service provider computer before syncing the institution node. In some examples, syncing the data node and the category node occurs prior to syncing the institution node.

In some examples, the data node may be a first data node. The process 1200 may further include generating a second data node in accordance with the configuration file. The second data node may be identified by a fifth unique data identifier and encrypted using a fifth cryptographic key. In this example, the category node further includes the fifth unique data identifier and the fifth cryptographic key.

Figure 13:
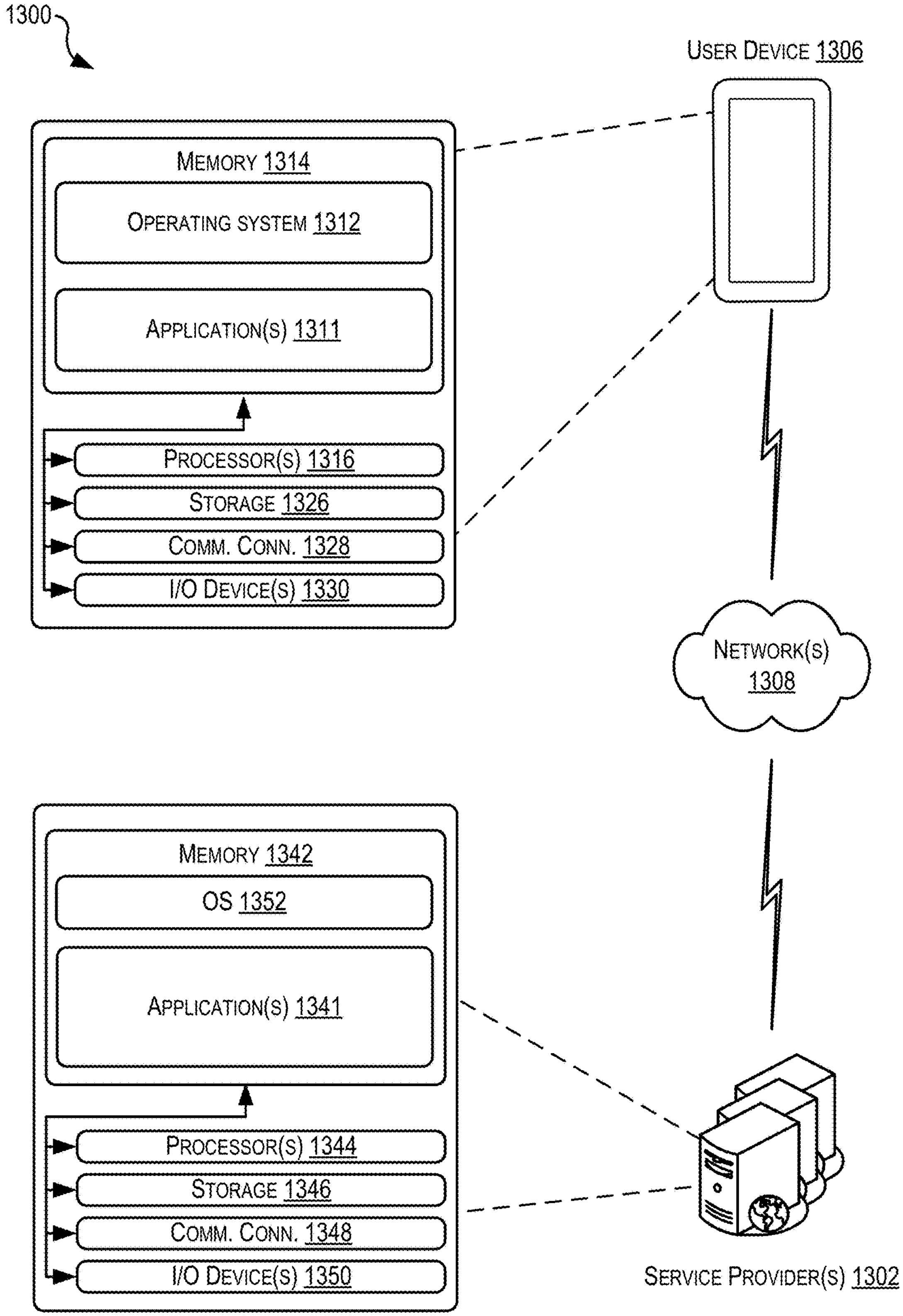
FIG. 13 illustrates a simplified block diagram depicting an example architecture for implementing the techniques described herein, according to at least one example.

FIG. 13 illustrates an example architecture or environment 1300 configured to implement techniques described herein, according to at least one example. In some examples, the example architecture 1300 may further be configured to enable a user device 1306 and service provider computer 1302 to share information. The service provider computer 1302 is an example of the service provider 104 and the EHR system 108. The user device 1306 is an example of the user devices 106 and 240. In some examples, the devices may be connected via one or more networks 1308 (e.g., via Bluetooth, WiFi, the Internet). In some examples, the service provider computer 1302 may be configured to implement at least some of the techniques described herein with reference to the user device 1306 and vice versa.

In some examples, the networks 1308 may include any one or a combination of many different types of networks, such as cable networks, the Internet, wireless networks, cellular networks, satellite networks, other private and/or public networks, or any combination thereof. While the illustrated example represents the user device 1306 accessing the service provider computer 1302 via the networks 1308, the described techniques may equally apply in instances where the user device 1306 interacts with the service provider computer 1302 over a landline phone, via a kiosk, or in any other manner. It is also noted that the described techniques may apply in other client/server arrangements (e.g., set-top boxes), as well as in non-client/server arrangements (e.g., locally stored applications, peer-to-peer configurations).

As noted above, the user device 1306 may be any type of computing device such as, but not limited to, a mobile phone, a smartphone, a personal digital assistant (PDA), a laptop computer, a desktop computer, a thin-client device, a tablet computer, a wearable device such as a smart watch, or the like. In some examples, the user device 1306 may be in communication with the service provider computer 1302 via the network 1308, or via other network connections.

In one illustrative configuration, the user device 1306 may include at least one memory 1314 and one or more processing units (or processor(s)) 1316. The processor(s) 1316 may be implemented as appropriate in hardware, computer-executable instructions, firmware, or combinations thereof. Computer-executable instruction or firmware implementations of the processor(s) 1316 may include computer-executable or machine-executable instructions written in any suitable programming language to perform the various functions described. The user device 1306 may also include geo-location devices (e.g., a global positioning system (GPS) device or the like) for providing and/or recording geographic location information associated with the user device 1306.

The memory 1314 may store program instructions that are loadable and executable on the processor(s) 1316, as well as data generated during the execution of these programs. Depending on the configuration and type of the user device 1306, the memory 1314 may be volatile (such as random access memory (RAM)) and/or non-volatile (such as read-only memory (ROM), flash memory, etc.). The user device 1306 may also include additional removable storage and/or non-removable storage 1326 including, but not limited to, magnetic storage, optical disks, and/or tape storage. The disk drives and their associated non-transitory computer-readable media may provide non-volatile storage of computer-readable instructions, data structures, program modules, and other data for the computing devices. In some implementations, the memory 1314 may include multiple different types of memory, such as static random access memory (SRAM), dynamic random access memory (DRAM), or ROM. While the volatile memory described herein may be referred to as RAM, any volatile memory that would not maintain data stored therein once unplugged from a host and/or power would be appropriate.

The memory 1314 and the additional storage 1326, both removable and non-removable, are all examples of non-transitory computer-readable storage media. For example, non-transitory computer-readable storage media may include volatile or non-volatile, removable or non-removable media implemented in any method or technology for storage of information such as computer-readable instructions, data structures, program modules, or other data. The memory 1314 and the additional storage 1326 are both examples of non-transitory computer-storage media. Additional types of computer-storage media that may be present in the user device 1306 may include, but are not limited to, phase-change RAM (PRAM), SRAM, DRAM, RAM, ROM, Electrically Erasable Programmable Read-Only Memory (EEPROM), flash memory or other memory technology, compact disc read-only memory (CD-ROM), digital video disc (DVD) or other optical storage, magnetic cassettes, magnetic tape, magnetic disk storage or other magnetic storage devices, or any other medium that can be used to store the desired information and that can be accessed by the user device 1306. Combinations of any of the above should also be included within the scope of non-transitory computer-readable storage media. Alternatively, computer-readable communication media may include computer-readable instructions, program modules, or other data transmitted within a data signal, such as a carrier wave, or other transmission. However, as used herein, computer-readable storage media does not include computer-readable communication media.

The user device 1306 may also contain communications connection(s) 1328 that allow the user device 1306 to communicate with a data store, another computing device or server, user terminals, and/or other devices via the network 1308. The user device 1306 may also include I/O device(s) 1330, such as a keyboard, a mouse, a pen, a voice input device, a touch screen input device, a display, speakers, a printer, etc.

Turning to the contents of the memory 1314 in more detail, the memory 1314 may include an operating system 1313 and/or one or more application programs or services for implementing the features disclosed herein such as applications 1311 (e.g., health application 222, digital wallet, third-party applications, browser application). In some examples, the applications 1311 may include a health application (e.g., the health application 222) to perform similar techniques as described with reference to the user device 1306. Similarly, at least some techniques described with reference to the service provider computer 1302 may be performed by the user device 1306.

The service provider computer 1302 may also be any type of computing device such as, but not limited to, a collection of virtual or "cloud" computing resources, a remote server, a mobile phone, a smartphone, a PDA, a laptop computer, a desktop computer, a thin-client device, a tablet computer, a wearable device, a server computer, or a virtual machine instance. In some examples, the service provider computer 1302 may be in communication with the user device 1306 via the network 1308, or via other network connections.

In one illustrative configuration, the service provider computer 1302 may include at least one memory 1342 and one or more processing units (or processor(s)) 1344. The processor(s) 1344 may be implemented as appropriate in hardware, computer-executable instructions, firmware, or combinations thereof. Computer-executable instruction or firmware implementations of the processor(s) 1344 may include computer-executable or machine-executable instructions written in any suitable programming language to perform the various functions described.

The memory 1342 may store program instructions that are loadable and executable on the processor(s) 1344, as well as data generated during the execution of these programs. Depending on the configuration and type of service provider computer 1302, the memory 1342 may be volatile (such as RAM) and/or non-volatile (such as ROM, flash memory, etc.). The service provider computer 1302 may also include additional removable storage and/or non-removable storage 1346 including, but not limited to, magnetic storage, optical disks, and/or tape storage. The disk drives and their associated non-transitory computer-readable media may provide non-volatile storage of computer-readable instructions, data structures, program modules, and other data for the computing devices. In some implementations, the memory 1342 may include multiple different types of memory, such as SRAM, DRAM, or ROM. While the volatile memory described herein may be referred to as RAM, any volatile memory that would not maintain data stored therein, once unplugged from a host and/or power, would be appropriate. The memory 1342 and the additional storage 1346, both removable and non-removable, are both additional examples of non-transitory computer-readable storage media.

The service provider computer 1302 may also contain communications connection(s) 1348 that allow the service provider computer 1302 to communicate with a data store, another computing device or server, user terminals, and/or other devices via the network 1308. The service provider computer 1302 may also include I/O device(s) 1350, such as a keyboard, a mouse, a pen, a voice input device, a touch input device, a display, speakers, a printer, etc.

Turning to the contents of the memory 1342 in more detail, the memory 1342 may include an operating system 1352 and/or one or more application programs 1341 or services for implementing the features disclosed herein including a provider service 210, the provider admin 212, the subscription service 220, the test harness 216, the device authentication service 226, the data storage engine 228, the data retrieval engine 234, the assets engine 236, the EHR authentication service 238, and/or the dashboard 242.

In the following, further examples are described to facilitate the understanding of the present disclosure.

Example 1. In this example, there is provided a computer-implemented method, including:
- encrypting, by a mobile user device using a plurality of cryptographic keys, health data associated with a user account of the mobile user device;
- storing the encrypted health data on the mobile user device using a multi-node data storage structure, with each node of the multi-node data structure being identified by a unique data identifier;
- sending the encrypted health data to a service provider that stores the encrypted health data according to the multi-node data storage structure, the unique data identifier identifying at least one node of the multi-node data storage structure;
- receiving a selection of a health institution to receive at least a portion of the health data; and
- based at least in part on the selection, sending at least one cryptographic key of the plurality of cryptographic keys and a data identifier corresponding to the multi-node storage structure to an electronic health record system associated with the health institution, the electronic health record system enabled to use the at least one cryptographic key and the data identifier to access and decrypt the portion of the health data from the service provider.

Example 2. In this example, there is provided a computer-implemented method of any of the preceding or subsequent examples, wherein encrypting the health data, storing the encrypted health data, and sending the encrypted health data are responsive to receiving the selection of the health institution, the selection representing a request to share the portion of the health data with the health institution.

Example 3. In this example, there is provided a computer-implemented method of any of the preceding or subsequent examples, wherein encrypting the health data includes encrypting each node of the multi-node storage structure using a unique cryptographic key of the plurality of cryptographic keys.

Example 4. In this example, there is provided a computer-implemented method of any of the preceding or subsequent examples, wherein the health data includes clinical health record data and sensor data.

Example 5. In this example, there is provided a computer-implemented method of any of the preceding or subsequent examples, wherein the clinical health record data is received from the electronic health record system or from a different health record system associated with a different health institution, and the sensor data is generated by a sensor of the mobile user device or received from a different user device associated with the mobile user device.

Example 6. In this example, there is provided a computer-implemented method of any of the preceding or subsequent examples, wherein a first portion of the health data is obtained by the mobile user device from the electronic health record system.

Example 7. In this example, there is provided a computer-implemented method of any of the preceding or subsequent examples, wherein a second portion of the health data is obtained by the mobile user device from a different electronic health record system associated with a different health institution.

Example 8. In this example, there is provided a computer-implemented method of any of the preceding or subsequent examples, wherein the health data is organized into a plurality of categories, and wherein the multi-node data storage structure includes a root node that represents the health institution and a plurality of branch nodes corresponding to each of the plurality of categories.

Example 9. In this example, there is provided a computer-implemented method of any of the preceding or subsequent examples, further including:

receiving, as a user input, information identifying a category of the health data; and determining the portion of the health data based at least in part on the category.

Example 10. In this example, there is provided a computer-implemented method of any of the preceding or subsequent examples, wherein the data identifier is unique to the health institution.

Example 11. In this example, there is provided a computer-implemented method of any of the preceding or subsequent examples, wherein the data identifier is a first data identifier of a plurality of data identifiers maintained by the mobile user device and corresponding to the multi-node storage structure, and wherein individual data identifiers of the plurality of data identifiers are associated with at least one of a particular health institution, a particular category of health data, or a predefined data range corresponding to a respective category of health data.

Example 12. In this example, there is provided a computer-implemented method of any of the preceding or subsequent examples, wherein individual cryptographic keys of the plurality of cryptographic keys are associated with at least one of a particular health institution, a particular category of health data, or a predefined range corresponding to a respective category of health data.

Example 13. In this example, there is provided an apparatus, including:

a memory including computer-executable instructions; and one or more processors in communication with the memory and configured to access the memory and execute the computer-executable instructions to perform the method of any of the preceding examples.

Example 14. In this example, there is provided one or more computer-readable storage devices including computer-executable instructions that, when executed by one or more processors, cause the one or more processors to perform the method of any one of claims of the preceding claims.

Example 15. In this example, there is provided a mobile user device, including:

a memory including computer-executable instructions; and a processor configured to access the memory and execute the computer-executable instructions to at least:

send encrypted health data to a service provider that stores the encrypted health data according to a multi-node data storage structure, the encrypted health data stored on the mobile user device according to a first version of the multi-node data storage structure;

receive a selection of a health institution to receive at least a portion of the health data; and based at least in part on the selection, send a cryptographic key and a data identifier that identifies a storage node of the first version of the multi-node storage structure to an electronic health record system associated with the health institution, the electronic health record system enabled to use the cryptographic key and the data identifier to access and decrypt the portion health data stored by the service provider at the storage node.

Example 16. In this example, there is provided a mobile user device of any of the preceding or subsequent examples, wherein the storage node stores a plurality of other cryptographic keys and a plurality of other unique data identifiers.

Example 17. In this example, there is provided a mobile user device of any of the preceding or subsequent examples, wherein the plurality of other unique data identifiers correspond to a plurality of categories of health data, each of which has its own node in the first and second versions of the multi-node data storage structure.

Example 18. In this example, there is provided a mobile user device of any of the preceding or subsequent examples, further including a display, and wherein the memory includes additional computer-executable instructions that, when executed by the processor, provide a user interface for presentation at the display, the user interface presenting a list of health institutions including the health institution.

Example 19. In this example, there is provided a mobile user device of any of the preceding or subsequent examples, wherein receiving the selection includes receiving, via the user interface, a user selection of the health institution from the list of health institutions.

Example 20. In this example, there is provided a mobile user device of any of the preceding or subsequent examples, wherein the memory includes additional computer-executable instructions that, when executed by the processor, encrypt, prior to sending the encrypted health data, the health data using the cryptographic key.

Example 21. In this example, there is provided a mobile user device of any of the preceding or subsequent examples, wherein sending the cryptographic key to the electronic health record system includes sending the cryptographic key to the electronic health record system without sharing the cryptographic key with the service provider.

Example 22. In this example, there is provided a computer-implemented method, including:

receiving an upload request from a mobile user device, the upload request including encrypted health record data and a set of unique data identifiers corresponding to the encrypted health record data;

storing, in a secure storage, the encrypted health record data in accordance with the set of unique data identifiers;

receiving a query from an electronic health record system associated with a health institution, the query including at least one unique data identifier of the set of unique data identifiers;

retrieving, from the secure storage using the at least one unique data identifier, the encrypted health record data; and sending the encrypted health record data for viewing by the electronic health record system of the health institution system.

Example 23. In this example, there is provided a computer-implemented method of any of the preceding or subsequent examples, wherein sending the encrypted health record data for viewing by the electronic health record system includes sending the encrypted health record data without sending cryptographic keys for decrypting the encrypted health record data.

Example 24. In this example, there is provided an apparatus, including:

a memory including computer-executable instructions; and one or more processors in communication with the memory and configured to access the memory and execute the computer-executable instructions to perform the method of any one of the examples 22-23.

Example 25. In this example, there is provided one or more computer-readable storage devices including computer-executable instructions that, when executed by one or more processors, cause the one or more processors to perform the method of any one of the examples 22-23.

Example 26. In this example, there is provided a computer-implemented method, including:

generating a data node of a multi-node data structure in accordance with a configuration file, the data node identified by a first unique data identifier and encrypted using a first cryptographic key, the data node including health data;

generating a category node of the multi-node data structure in accordance with the configuration file, the category node including the first unique data identifier and the first cryptographic key, the category node identified by a second unique data identifier and encrypted using a second cryptographic key;

generating an institution node of the multi-node data structure in accordance with the configuration file, the institution node including the second unique data identifier and the second cryptographic key, the institution node identified by a third unique data identifier and encrypted using a third cryptographic key; and sharing the data node, the category node, and the institution node with a service provider.

Example 27. In this example, there is provided a computer-implemented method of any of the preceding or subsequent examples, wherein the multi-node data structure is usable for other systems to query health data represented by the multi-node.

Example 28. In this example, there is provided a computer-implemented method of any of the preceding or subsequent examples, further including dynamically generating a set queries based at least in part on the configuration file, and wherein generating the data node in accordance with the configuration file includes executing at least one query of the set of queries to collect a set of health data to populate the data node.

Example 29. In this example, there is provided a computer-implemented method of any of the preceding or subsequent examples, wherein the configuration file identifies one or more required ranges corresponding to the set of health data.

Example 30. In this example, there is provided a computer-implemented method of any of the preceding or subsequent examples, further including determining that each of generating the data node, generating the category node, and generating the institution node was successful.

Example 31. In this example, there is provided a computer-implemented method of any of the preceding or subsequent examples, further including, after determining that each of generating the data node, generating the category node, and generating the institution node was successful, sending the third unique data identifier and the third cryptographic key to an electronic health record system associated with a health institution.

Example 32. In this example, there is provided a computer-implemented method of any of the preceding or subsequent examples, further including:

receiving a request to share health data with a health institution; and responsive to the request, sending the third unique data identifier and the third cryptographic key to an electronic health record system associated with the health institution.

Example 33. In this example, there is provided a computer-implemented method of any of the preceding or subsequent examples, wherein sending the third unique data identifier and the third cryptographic key to the electronic health record system includes sending without sending other unique data identifiers or other cryptographic keys.

Example 34. In this example, there is provided a computer-implemented method of any of the preceding or subsequent examples, wherein the third unique data identifier includes a hash that represents data of the institution node including the second unique data identifier and the second cryptographic key.

Example 35. In this example, there is provided a computer-implemented method of any of the preceding or subsequent examples, further including generating the third unique data identifier by hashing data representing the second unique data identifier and the second cryptographic key.

Example 36. In this example, there is provided a computer-implemented method of any of the preceding or subsequent examples, wherein the institution node is a first institution node, the method further includes generating a second institution node of the multi-node data structure in accordance with the configuration file, the second institution node including the second unique data identifier and the second cryptographic key, the second institution node identified by a fourth unique identifier and encrypted using a fourth cryptographic key.

Example 37. In this example, there is provided a computer-implemented method of any of the preceding or subsequent examples, wherein the institution node is a first institution node, the category node is a first category node, and the data node is a first data node, and wherein the method further includes:

generating a second data node of the multi-node data structure in accordance with the configuration file, the second data node identified by a fourth unique identifier and encrypted using a fourth cryptographic key;

generating a second category node of the multi-node data structure in accordance with the configuration file, the second category node including (i) the first unique data identifier, (ii) the first cryptographic key, (iii) the fourth unique identifier, and the (iv) the fourth cryptographic key, the second category node identified by a fifth data identifier and encrypted using a fifth cryptographic key; and generating a second institution node of the multi-node data structure in accordance with the configuration file, the second institution node including (i) the second unique data identifier, (ii) the second cryptographic key, (iii) the fifth data identifier, and (iv) the fifth cryptographic key, the second institution node identified by a sixth unique data identifier and encrypted using a sixth cryptographic key.

Example 38. In this example, there is provided a computer-implemented method of any of the preceding or subsequent examples, further including deleting the first institution node and the first category node.

Example 39. In this example, there is provided a computer-implemented method of any of the preceding or subsequent examples, further including sending a deletion request to the service provider to delete the first institution node and the first category node from storage of the service provider.

Example 40. In this example, there is provided a computer-implemented method of any of the preceding or subsequent examples, wherein sharing the data node, the category node, and the institution node with the service provider includes syncing the data node, the category node, and the institution node with the service provider computer before syncing the institution node.

Example 41. In this example, there is provided a computer-implemented method of any of the preceding or subsequent examples, wherein syncing of the data node and the category node occurs prior to syncing of the institution node.

Example 42. In this example, there is provided a computer-implemented method of any of the preceding or subsequent examples, wherein the data node is a first data node, and wherein the method further includes generating a second data node in accordance with the configuration file, the second data node identified by a fifth unique data identifier and encrypted using a fifth cryptographic key, and wherein the category node further includes the fifth unique data identifier and the fifth cryptographic key.

Example 43. In this example, there is provided an apparatus, including:

a memory including computer-executable instructions; and one or more processors in communication with the memory and configured to access the memory and execute the computer-executable instructions to perform the method of any of examples 26-42.

Example 44. In this example, there is provided one or more computer-readable storage devices including computer-executable instructions that, when executed by one or more processors, cause the one or more processors to perform the method of any one of examples 26-42.

The various examples can be further implemented in a wide variety of operating environments, which in some cases can include one or more user computers, computing devices, or processing devices which can be used to operate any of a number of applications. User or client devices can include any of a number of general purpose personal computers, such as desktop or laptop computers running a standard operating system, as well as cellular, wireless, and handheld devices running mobile software and capable of supporting a number of networking and messaging protocols. Such a system also can include a number of workstations running any of a variety of commercially-available operating systems and other known applications for purposes such as development and database management. These devices also can include other electronic devices, such as dummy terminals, thin-clients, gaming systems, and other devices capable of communicating via a network.

Most examples utilize at least one network that would be familiar to those skilled in the art for supporting communications using any of a variety of commercially-available protocols, such as TCP/IP, OSI, FTP, UPnP, NFS, CIFS, and AppleTalk. The network can be, for example, a local area network, a wide-area network, a virtual private network, the Internet, an intranet, an extranet, a public switched telephone network, an infrared network, a wireless network, and any combination thereof.

In examples utilizing a network server, the network server can run any of a variety of server or mid-tier applications, including HTTP servers, FTP servers, CGI servers, data servers, Java servers, and business application servers. The server(s) may also be capable of executing programs or scripts in response to requests from user devices, such as by executing one or more applications that may be implemented as one or more scripts or programs written in any programming language, such as Java®, C, C# or C++, or any scripting language, such as Perl, Python, or TCL, as well as combinations thereof. The server(s) may also include database servers, including without limitation those commercially available from Oracle®, Microsoft®, Sybase®, and IBM®.

The environment can include a variety of data stores and other memory and storage media as discussed above. These can reside in a variety of locations, such as on a storage medium local to (and/or resident in) one or more of the computers or remote from any or all of the computers across the network. In a particular set of examples, the information may reside in a storage-area network (SAN) familiar to those skilled in the art. Similarly, any necessary files for performing the functions attributed to the computers, servers, or other network devices may be stored locally and/or remotely, as appropriate. Where a system includes computerized devices, each such device can include hardware elements that may be electrically coupled via a bus, the elements including, for example, at least one central processing unit (CPU), at least one input device (e.g., a mouse, keyboard, controller, touch screen, or keypad), and at least one output device (e.g., a display device, printer, or speaker).

Such a system may also include one or more storage devices, such as disk drives, optical storage devices, and solid-state storage devices such as RAM or ROM, as well as removable media devices, memory cards, flash cards, etc.

Such devices can also include a computer-readable storage media reader, a communications device (e.g., a modem, a network card (wireless or wired), an infrared communication device), and working memory as described above. The computer-readable storage media reader can be connected with, or configured to receive, a non-transitory computer-readable storage medium, representing remote, local, fixed, and/or removable storage devices as well as storage media for temporarily and/or more permanently containing, storing, transmitting, and retrieving computer-readable information. The system and various devices also typically will include a number of software applications, modules, services, or other elements located within at least one working memory device, including an operating system and application programs, such as a client application or browser. It should be appreciated that alternate examples may have numerous variations from that described above. For example, customized hardware might also be used and/or particular elements might be implemented in hardware, software (including portable software, such as applets), or both. Further, connection to other computing devices such as network input/output devices may be employed.

Non-transitory storage media and computer-readable media for containing code, or portions of code, can include any appropriate media known or used in the art, including storage media, such as, but not limited to, volatile and non-volatile, removable and non-removable media implemented in any method or technology for storage of information such as computer-readable instructions, data structures, program modules, or other data, including RAM, ROM, EEPROM, flash memory or other memory technology, CD-ROM, DVD or other optical storage, magnetic cassettes, magnetic tape, magnetic disk storage or other magnetic storage devices, or any other medium which can be used to store the desired information and which can be accessed by a system device. Based at least in part on the disclosure and teachings provided herein, a person of ordinary skill in the art will appreciate other ways and/or methods to implement the various examples.

The specification and drawings are, accordingly, to be regarded in an illustrative rather than a restrictive sense. It will, however, be evident that various modifications and changes may be made thereunto without departing from the broader spirit and scope of the disclosure as set forth in the claims.

Other variations are within the spirit of the present disclosure. Thus, while the disclosed techniques are susceptible to various modifications and alternative constructions, certain illustrated examples thereof are shown in the drawings and have been described above in detail. It should be understood, however, that there is no intention to limit the disclosure to the specific form or forms disclosed, but on the contrary, the intention is to cover all modifications, alternative constructions and equivalents falling within the spirit and scope of the disclosure, as defined in the appended claims.

The use of the terms "a" and "an" and "the" and similar referents in the context of describing the disclosed examples (especially in the context of the following claims) are to be construed to cover both the singular and the plural, unless otherwise indicated herein or clearly contradicted by context. The terms "comprising," "having," "including," and "containing" are to be construed as open-ended terms (e.g., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate examples of the disclosure and does not pose a limitation on the scope of the disclosure unless otherwise claimed. No language in the specification should be construed as indicating any non-claimed element as essential to the practice of the disclosure.

Disjunctive language such as the phrase "at least one of X, Y, or Z," unless specifically stated otherwise, is otherwise understood within the context as used in general to present that an item, term, etc., may be either X, Y, or Z, or any combination thereof (e.g., X, Y, and/or Z). Thus, such disjunctive language is not generally intended to, and should not, imply that certain examples require at least one of X, at least one of Y, or at least one of Z to each be present.

Preferred examples of this disclosure are described herein, including the best mode known to the inventors for carrying out the disclosure. Variations of those preferred examples may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

As described above, one aspect of the present technology is the gathering and use of data available from various sources to provide a comprehensive and complete window to a user's personal health record. The present disclosure contemplates that in some instances, this gathered data may include personally identifiable information (PII) data that uniquely identifies or can be used to contact or locate a specific person. Such personal information data can include demographic data, location-based data, telephone numbers, email addresses, Twitter ID's, home addresses, data or records relating to a user's health or level of fitness (e.g., vital sign measurements, medication information, exercise information), date of birth, health record data, or any other identifying or personal or health information.

The present disclosure recognizes that the use of such personal information data, in the present technology, can be used to the benefit of users. For example, the personal information data can be used to provide enhancements to a user's personal health record. Further, other uses for personal information data that benefit the user are also contemplated by the present disclosure. For instance, health and fitness data may be used to provide insights into a user's general wellness, or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the U.S., collection of or access to certain health data may be governed by federal and/or state laws, such as the Health Insurance Portability and Accountability Act (HIPAA); whereas health data in other countries may be subject to other regulations and policies and should be handled accordingly. Hence different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of advertisement delivery services or other services relating to health record management, the present technology can be configured to allow users to select to "opt in" or "opt out" of participation in the collection of personal information data during registration for services or anytime thereafter. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth), controlling the amount or specificity of data stored (e.g., collecting location data at a city level rather than at an address level), controlling how data is stored (e.g., aggregating data across users), and/or other methods.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data.

What is claimed is:

1. A computer-implemented method, comprising:

receiving an upload request from a mobile user device, the upload request comprising encrypted health record data and a set of unique data identifiers corresponding to the encrypted health record data;

storing, in a secure storage, the encrypted health record data in accordance with the set of unique data identifiers;

receiving a query from an electronic health record system associated with a health institution, the query comprising at least one unique data identifier of the set of unique data identifiers, wherein each unique identifier of the set of unique data identifiers corresponds to at least one node of a multi-node data structure;

retrieving, from the secure storage using the at least one unique data identifier, the encrypted health record data; and sending the encrypted health record data for viewing by the electronic health record system of the health institution.

2. The computer-implemented method of claim 1, wherein sending the encrypted health record data for viewing by the electronic health record system comprises sending the encrypted health record data without sending cryptographic keys for decrypting the encrypted health record data.

3. The computer-implemented method of claim 1, further comprising:

receiving a user identifying information element from the mobile user device; and authenticating, based on the user identifying information element, that the mobile user device is an approved user device.

4. The computer-implemented method of claim 3, wherein the approved user device is one of a user device of a particular model, a user device operating a specific operating system, a user device operating a specific version of an operating system, or a user device operating a particular application.

5. The computer-implemented method of claim 3, wherein the user identifying information element includes a device identifier, and wherein authenticating the mobile user device includes checking that the approved user device is on a list of authorized devices.

6. The computer-implemented method of claim 1, further comprising:

receiving a health institution identifying information element from the electronic health record system; and authenticating, based on the health institution identifying information element, that the electronic health record system is an approved health institution device.

7. A system, comprising:

a memory comprising computer-executable instructions; and one or more processors in communication with the memory and configured to access the memory and execute the computer-executable instructions to at least:

receive a user identifying information element from a mobile user device;

authenticate, based on the user identifying information element, that the mobile user device is an approved user device;

receive an upload request from the mobile user device, the upload request comprising encrypted health record data and a set of unique data identifiers corresponding to the encrypted health record data;

store, in a secure storage, the encrypted health record data in accordance with the set of unique data identifiers;

receive a query from an electronic health record system associated with a health institution, the query comprising at least one unique data identifier of the set of unique data identifiers;

retrieve, from the secure storage using the at least one unique data identifier, the encrypted health record data; and send the encrypted health record data for viewing by the electronic health record system of the health institution.

8. The system of claim 7, wherein sending the encrypted health record data for viewing by the electronic health record system comprises sending the encrypted health record data without sending cryptographic keys for decrypting the encrypted health record data.

9. The system of claim 7, wherein each unique identifier of the set of unique data identifiers corresponds to at least one node of a multi-node data structure.

10. The system of claim 7, wherein the approved user device is one of a user device of a particular model, a user device operating a specific operating system, a user device operating a specific version of an operating system, or a user device operating a particular application.

11. The system of claim 7, wherein the user identifying information element includes a device identifier, and wherein authenticating the mobile user device includes checking that the approved user device is on a list of authorized devices.

12. The system of claim 7, further comprising:

receiving a health institution identifying information element from the electronic health record system; and authenticating, based on the health institution identifying information element, that the electronic health record system is an approved health institution device.

13. One or more non-transitory computer-readable media comprising computer-executable instructions that, when executed by one or more processors, cause the one or more processors to perform operations, comprising:

receiving an upload request from a mobile user device, the upload request comprising encrypted health record data and a set of unique data identifiers corresponding to the encrypted health record data;

storing, in a secure storage, the encrypted health record data in accordance with the set of unique data identifiers;

receiving a query from an electronic health record system associated with a health institution, the query comprising at least one unique data identifier of the set of unique data identifiers, wherein each unique identifier of the set of unique data identifiers corresponds to at least one node of a multi-node data structure;

retrieving, from the secure storage using the at least one unique data identifier, the encrypted health record data; and sending the encrypted health record data for viewing by the electronic health record system of the health institution.

14. The one or more non-transitory computer-readable media of claim 13, wherein sending the encrypted health record data for viewing by the electronic health record system comprises sending the encrypted health record data without sending cryptographic keys for decrypting the encrypted health record data.

15. The one or more non-transitory computer-readable media of claim 13, further comprising:

receiving a user identifying information element from the mobile user device; and authenticating, based on the user identifying information element, that the mobile user device is an approved user device.

16. The one or more non-transitory computer-readable media of claim 15, wherein the approved user device is one of a user device of a particular model, a user device operating a specific operating system, a user device operating a specific version of an operating system, a user device operating a particular application, or a user device on a list of authorized devices.

17. The one or more non-transitory computer-readable media of claim 13, further comprising:

receiving a health institution identifying information element from the electronic health record system; and authenticating, based on the health institution identifying information element, that the electronic health record system is an approved health institution device.

* * * * *